US010820802B2

(12) United States Patent
Meyerson et al.

(10) Patent No.: US 10,820,802 B2
(45) Date of Patent: Nov. 3, 2020

(54) WEARABLE PATCH FOR PATIENT MONITORING

(71) Applicant: Welch Allyn, Inc., Skaneateles Falls, NY (US)

(72) Inventors: Craig M. Meyerson, Syracuse, NY (US); David E. Quinn, Auburn, NY (US); Kenzi L. Mudge, Syracuse, NY (US); Zhon Ye Chu, Syracuse, NY (US); Michael T. McMahon, Syracuse, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 618 days.

(21) Appl. No.: 15/395,324

(22) Filed: Dec. 30, 2016

(65) Prior Publication Data

US 2018/0184902 A1 Jul. 5, 2018

(51) Int. Cl.
*A61B 5/00* (2006.01)
*A61B 5/01* (2006.01)
*G01K 13/00* (2006.01)

(52) U.S. Cl.
CPC .......... *A61B 5/0008* (2013.01); *A61B 5/01* (2013.01); *A61B 5/68335* (2017.08); *A61B 5/0002* (2013.01); *A61B 5/6833* (2013.01); *A61B 2560/0412* (2013.01); *A61B 2562/04* (2013.01); *A61B 2562/043* (2013.01); *A61B 2562/046* (2013.01); *A61B 2562/164* (2013.01); *A61B 2562/166* (2013.01); *A61M 2230/50* (2013.01); *G01K 13/002* (2013.01)

(58) Field of Classification Search
CPC ..... A61B 5/0008; A61B 5/01; A61B 5/68335; A61B 2562/166; A61B 2562/164; A61B 2562/046; A61B 2560/0412; A61B 2562/04; A61B 2562/043; A61M 2230/04
See application file for complete search history.

(56) References Cited

U.S. PATENT DOCUMENTS

| | | | | |
|---|---|---|---|---|
| 5,749,365 A * | 5/1998 | Magill | ................ | A61B 5/1135 600/484 |
| 9,132,031 B2 * | 9/2015 | Levinson | .................. | A61F 7/10 |
| 9,332,918 B1 * | 5/2016 | Buckley | ............. | A61B 5/04001 |
| 9,483,726 B2 * | 11/2016 | Mei | ...................... | A61B 5/6814 |
| 9,808,170 B2 * | 11/2017 | Lane | .................. | A61B 5/04087 |
| 10,080,524 B1 * | 9/2018 | Xi | ............................ | A61B 5/01 |

(Continued)

FOREIGN PATENT DOCUMENTS

DE 10 2013 216 256 * 9/2014 ............... G01K 1/08

*Primary Examiner* — Sean P Dougherty
(74) *Attorney, Agent, or Firm* — Lee & Hayes, P.C.

(57) ABSTRACT

A patch includes a substrate, and a plurality of temperature sensors. Such sensors include a first temperature sensor, a second temperature sensor, a third temperature sensor connected to the substrate between the first temperature sensor and the second temperature sensor, and a fourth temperature sensor substantially overlaying the third temperature sensor. The patch also includes a layer of insulative material spacing the fourth temperature sensor from the third temperature sensor. In such examples, the patch also includes an antenna configured to transmit information associated with temperatures determined by the first, second, third, and fourth temperature sensors.

16 Claims, 13 Drawing Sheets

(56) References Cited

U.S. PATENT DOCUMENTS

| | | | |
|---|---|---|---|
| 2006/0058600 A1* | 3/2006 | Eichler | A61B 5/0536 600/407 |
| 2007/0206655 A1* | 9/2007 | Haslett | A61F 13/023 374/141 |
| 2009/0204100 A1* | 8/2009 | Van Pieterson | A61B 5/0008 604/503 |
| 2010/0298895 A1* | 11/2010 | Ghaffari | A61B 1/00082 607/3 |
| 2011/0051776 A1* | 3/2011 | Bieberich | G01K 1/165 374/163 |
| 2011/0158284 A1* | 6/2011 | Goto | A61B 5/01 374/163 |
| 2011/0190600 A1* | 8/2011 | McKenna | A61B 5/01 600/301 |
| 2011/0214602 A1* | 9/2011 | Park | G01K 3/04 116/216 |
| 2011/0249699 A1* | 10/2011 | Bieberich | G01K 1/165 374/1 |
| 2011/0249701 A1* | 10/2011 | Bieberich | G01K 13/002 374/163 |
| 2012/0242481 A1* | 9/2012 | Gernandt | G08B 21/0219 340/539.13 |
| 2012/0289855 A1* | 11/2012 | Bieberich | G01K 1/165 600/549 |
| 2013/0310661 A1* | 11/2013 | Jedwab | A61B 5/1107 600/301 |
| 2013/0333094 A1* | 12/2013 | Rogers | A61B 5/01 2/161.7 |
| 2014/0243681 A1* | 8/2014 | Hielscher | A61B 5/6807 600/473 |
| 2015/0245782 A1* | 9/2015 | Morland | A61B 5/065 600/301 |
| 2016/0062412 A1* | 3/2016 | Park | G06F 1/1616 361/679.27 |
| 2016/0149292 A1* | 5/2016 | Ganton | A61B 5/01 600/300 |
| 2017/0188841 A1* | 7/2017 | Ma | G16H 50/20 |
| 2017/0303815 A1* | 10/2017 | De Limon | A61B 5/4878 |
| 2017/0319100 A1* | 11/2017 | Holzhacker | A61B 5/053 |
| 2018/0092598 A1* | 4/2018 | Chen | A61B 5/6801 |
| 2018/0133499 A1* | 5/2018 | Dronov | A61N 1/403 |
| 2018/0153760 A1* | 6/2018 | Rosen | A61H 7/00 |
| 2018/0160909 A1* | 6/2018 | Damania | A61B 5/01 |
| 2018/0184902 A1* | 7/2018 | Meyerson | A61B 5/0008 |
| 2018/0249945 A1* | 9/2018 | Najafi | A61B 5/1038 |
| 2019/0000324 A1* | 1/2019 | Laugaard Nielsen | A61B 5/6833 |
| 2019/0175096 A1* | 6/2019 | Xi | A61B 5/441 |

\* cited by examiner

WEARABLE PATCH FOR PATIENT MONITORING

CROSS-REFERENCE TO RELATED APPLICATIONS

Not applicable.

STATEMENT REGARDING FEDERALLY SPONSORED RESEARCH OR DEVELOPMENT

None.

REFERENCE TO A "SEQUENCE LISTING"

Not applicable.

BACKGROUND OF THE INVENTION

Field of the Invention

The present disclosure generally relates to devices and methods for patient monitoring and, in particular, to wearable patches configured for use in determining a temperature of the patient.

Description of Related Art

Body temperature is widely used by physicians and other healthcare professionals as an indicator of a person's health. In most healthcare facilities, various non-invasive techniques may be utilized to measure temperature before, during, and/or after treatment. Such techniques typically include the use of oral, rectal, tympanic, or axial thermometers. These instruments are useful in providing a substantially instantaneous temperature reading, but are not generally used to provide continuous, relatively long-term monitoring of a patient's temperature. However, it is this continuous temperature measurement, or the determination of relatively sudden changes in patient temperature that is often useful to healthcare professionals when providing treatment. Such devices are not well-suited for continuous temperature measurement since, for example, disposing a thermometer in the mouth of a patient for long periods of time can cause discomfort and can be otherwise cumbersome. Moreover, often the condition of the patient may make it difficult or impossible to access, for example, the mouth, rectum, and/or other areas of the body where temperature is typically measured with such devices.

To overcome some of these problems, devices have been developed enabling continuous monitoring of patient temperature. Such devices are typically in the form of a removably attachable patch or bandage-like structure having one or more temperature sensors. Such devices are typically adhered to the patient's skin overlaying a portion of an artery or other blood vessel. These devices, however, are characterized by deficiencies making them undesirable for use in many patient treatment settings. For example, such devices must be placed in close proximity to a blood vessel in order to obtain an accurate temperature measurement. However, since such blood vessels are located beneath the skin, and are not easily visible, such devices are often mispositioned on the patient. Such mispositioning can reduce the accuracy of the temperature measurement obtained using such devices. In addition, the temperature at the skin surface can be significantly influenced by ambient temperature and often does not correlate well with patient temperature. Such known devices are typically not configured to account for the effect of ambient conditions when determining patient temperature.

The example embodiments of the present disclosure overcome one or more of the deficiencies described above. Additionally, the example embodiments of the present disclosure relate to example processes, systems, and/or devices disclosed in co-owned U.S. Pat. No. 8,657,758, the entire disclosure of which is expressly incorporated herein by reference.

BRIEF SUMMARY OF THE INVENTION

In an example embodiment of the present disclosure, a wearable patch includes a substrate and a plurality of temperature sensors. The plurality of temperature sensors includes a first temperature sensor connected to the substrate and disposed along a longitudinal axis of the substrate, and a second temperature sensor connected to the substrate, disposed along the longitudinal axis, and spaced from the first temperature sensor. The plurality of temperature sensors also includes a third temperature sensor connected to the substrate, and disposed along the longitudinal axis between the first temperature sensor and the second temperature sensor. The plurality of temperature sensors further includes a fourth temperature sensor substantially overlaying the third temperature sensor. The patch also includes a layer of electrically and/or thermally insulative material spacing the fourth temperature sensor from the third temperature sensor. Additionally, the patch includes an antenna configured to transmit information associated with temperatures determined by the first, second, third, and fourth temperature sensors. In some examples, the patch may also include one or more reference resistors associated with a temperature control circuit. In such examples, one or more of the temperature sensors described herein may use a differential reading across the reference resistor to compensate for variations in power delivered to the circuit.

In an additional embodiment of the present disclosure, a computer-readable storage device contains instructions that, when executed by a controller, cause the controller to perform operations. In such an example embodiment, the operations include determining a first temperature, of a skin surface of a patient, with a first temperature sensor of a wearable patch, wherein the first temperature is determined when the patch is disposed on the skin surface. In such examples, the patch further includes a substrate having a longitudinal axis, the first temperature sensor being connected to the substrate and disposed along the longitudinal axis. The patch also includes a second temperature sensor connected to the substrate, disposed along the longitudinal axis, and spaced from the first temperature sensor. The patch further includes a third temperature sensor connected to the substrate, and disposed along the longitudinal axis between the first temperature sensor and the second temperature sensor. Additionally, the patch includes a fourth temperature sensor substantially overlaying the third temperature sensor, and an antenna configured to transmit information associated with temperatures determined by the first, second, third, and fourth temperature sensors to the controller.

In such example embodiments, the operations also include determining a second temperature of the skin surface with the second temperature sensor when the patch is disposed on the skin surface, determining a third temperature of the skin surface with the third temperature when the patch is disposed on the skin surface, and determining a fourth temperature with the fourth temperature sensor when the patch is disposed on the skin surface, wherein the first, second, third, and fourth temperatures are determined substantially simultaneously. The operations further include determining a correction factor based on at least two of the first, second, third, and fourth temperatures, and determining a patient temperature based on the correction factor and the at least two of the first, second, third, and fourth temperatures.

In a further example embodiment of the present disclosure, a method of manufacturing a system includes providing a substrate including a longitudinal axis, a first side, and a second side opposite the first side. The method also includes connecting a first temperature sensor to the substrate along the longitudinal axis, connecting a second temperature sensor to the substrate along the longitudinal axis and spaced from the first temperature sensor, and connecting a third temperature sensor to the substrate along the longitudinal axis between the first temperature sensor and the second temperature sensor. The method further includes providing a fourth temperature sensor substantially overlaying the third temperature sensor. Additionally, the method includes providing an antenna at a fixed location relative to the substrate, the antenna being configured to transmit information associated with temperatures determined by the first, second, third, and fourth temperature sensors.

BRIEF DESCRIPTION OF THE SEVERAL VIEWS OF THE DRAWING(S)

Figure 15:
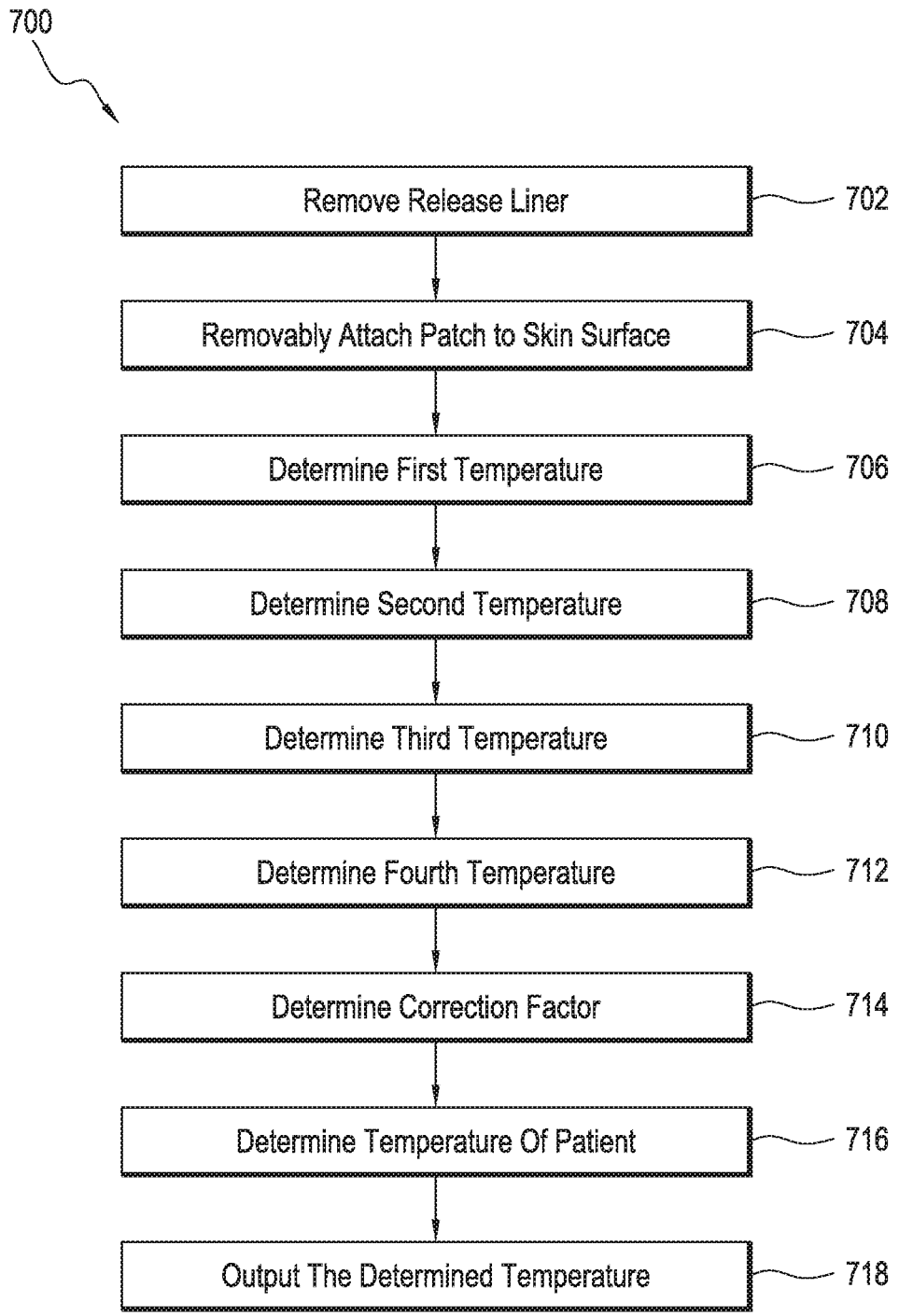

FIG. 15 includes a flowchart illustrating an example method of the present disclosure.

Figure 16:
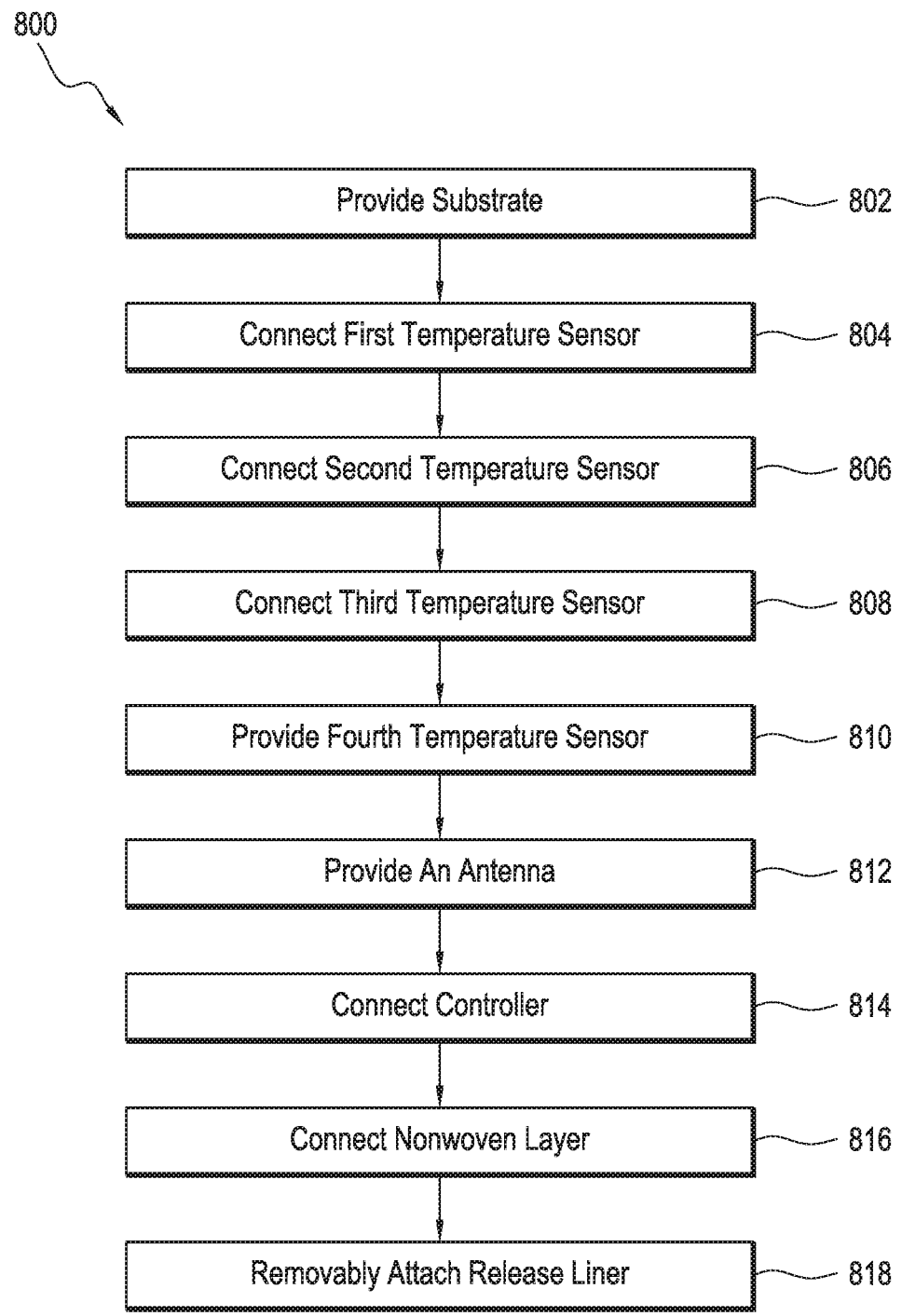

FIG. 16 includes a flowchart illustrating another example method of the present disclosure.

DETAILED DESCRIPTION OF THE INVENTION

Figure 1:
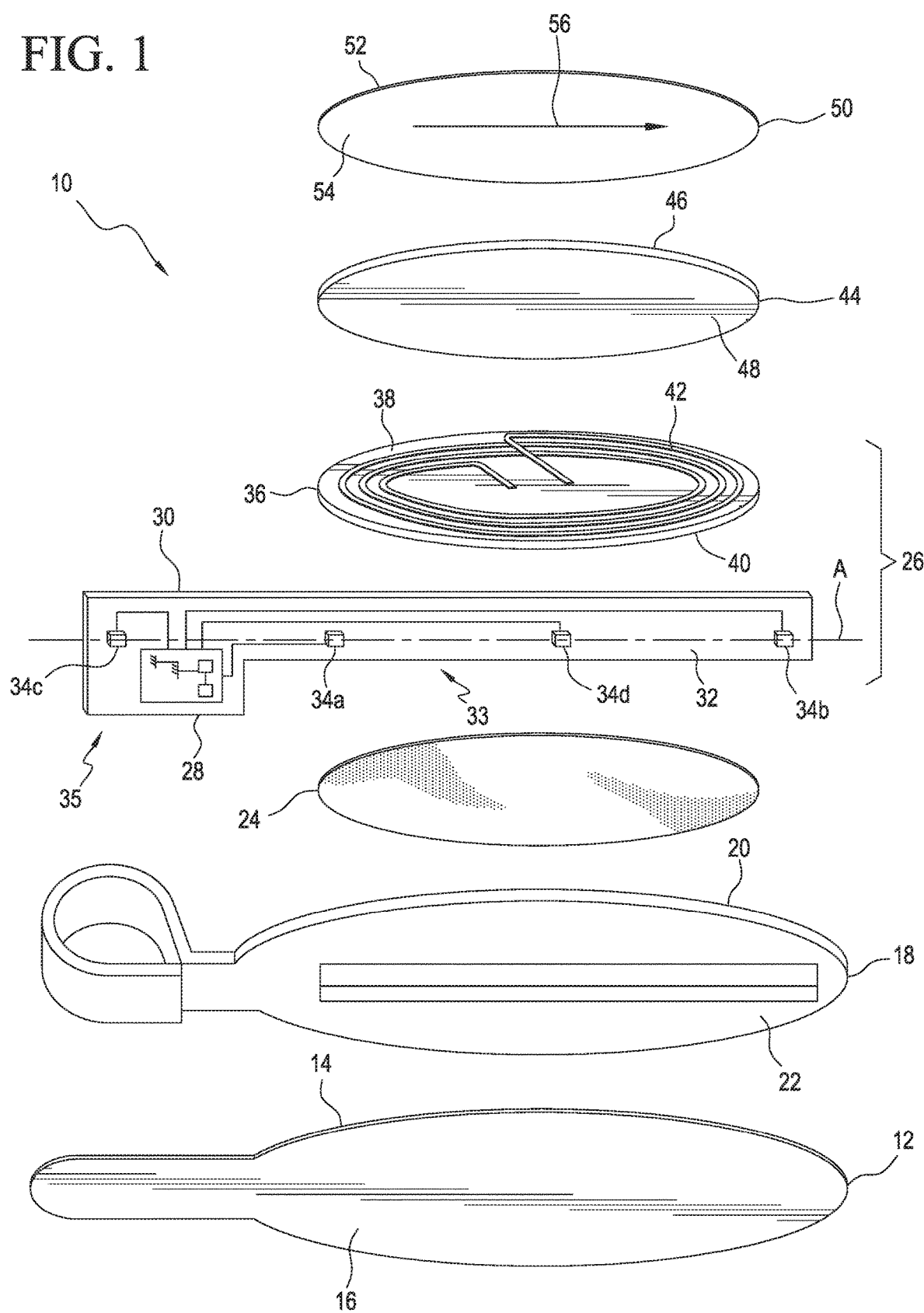
FIG. 1 is an exploded view of a patch according to an example embodiment of the present disclosure.

FIG. 1 illustrates an exploded view of an example patch 10 of the present disclosure. As will be described in detail below, the example patches of the present disclosure may be components of a patient monitoring system, a temperature determination system, and/or any other system configured to monitor a patient. In some examples, the patches and/or systems of the present disclosure may be configured to determine a temperature of the patient and/or any other hemodynamic parameter of the patient. As used herein, the term "hemodynamic parameter" can include any indication of cardiac or vascular health, such as, for example, an indication of cardiac, circulatory, or vascular functionality. In some examples, a hemodynamic parameter may include a heart rate, a blood pressure, a blood vessel compliance, an aortic index, an augmentation index, a reflected wave ratio, or an indication of treatment. Additionally, the temperatures sensed, measured, calculated, estimated, and/or otherwise determined by the example patches and/or other system components described herein may comprise skin surface temperatures, internal or "core" temperatures, and/or any other temperature of a patient. For purposes of the present disclosure, embodiments in which the patches and/or other system components are configured to determine one or more temperatures of a patient and/or a core temperature of the patient will be described below unless otherwise noted.

As shown in FIG. 1, an example patch 10 may include a variety of components including a release liner 12 having a first side 14 (e.g., a top) and a second side 16 (e.g., a bottom) disposed opposite the first side 14. The release liner 12 may be a substantially planar layer of the patch 10 that is removably attached to a skin surface-facing side of a nonwoven layer 18 of the patch 10. For example, the nonwoven layer 18 may include a first side 20 (e.g., a top) and a second side 22 (e.g., a bottom) disposed opposite the first side 20, and the release liner 12 may be removably attached to the second side 22 of the nonwoven layer 18. As will be described with respect to at least FIG. 7, a biocompatible adhesive may be disposed on at least a portion of the second side 22 of the nonwoven layer 18 in order to assist in removably attaching the patch 10 to a skin surface of a patient. In such examples, such an adhesive may at least temporarily adhere and/or otherwise releasably attach the first side 14 of the release liner 12 to the second side 22 of the nonwoven layer 18.

The release liner 12 may be made from any flexible medically approved material known in the art. For example, such materials may include plastics, rubber, polymers, synthetic materials, cloth, mesh, woven fabrics, nonwoven fabrics, and/or combinations thereof. For example, the release liner 12 may be made from materials similar to and/or the same as the release pads commonly found removably attached to the adhesive portions of conventional bandages. In some examples, at least a portion of the first side 14 may include a coating and/or other material that enables the release liner 12 to be relatively easily removed from the biocompatible adhesive disposed on the second side 22 of the nonwoven layer 18.

The nonwoven layer 18 may be made from any of the medically approved materials described above with respect to the release liner 12. For example, the nonwoven layer 18 and/or portions thereof may be made from nonwoven fabric and/or other materials similar to conventional removable bandages. These materials may allow for breathability during use of the patch 10 and for easy disposal of the patch 10 once use is complete. In addition, such materials may be substantially flexible, substantially light-weight, and/or relatively comfortable such that a patch 10 may be disposed on and/or removably attached to the skin surface of a patient for extended periods of time. It is understood that the nonwoven fabric and/or other materials used to form the nonwoven layer 18 may include fibers and/or other structural components that may wick away sweat and/or other fluids. As a result, such materials may reduce irritation associated with disposing the patch 10 on a skin surface for extended periods of time and may prolong adhesion of the second side 22 of the nonwoven layer 18 to the skin surface.

In some examples, the patch 10 may also include a base layer 24 disposed adjacent to and/or connected to the first side 20 of the nonwoven layer 18. In particular, the base layer 24 may include a top surface and a bottom surface opposite the top surface, and the top and bottom surfaces of the base layer 24 may each include an adhesive (e.g., a biocompatible adhesive) disposed thereon. The base layer 24 may be made from any of the materials described above with respect to the release liner 12 and the nonwoven layer 18. In some examples, the base layer 24 may be adhered to the first side 20 of the nonwoven layer 18, and may be configured to adhere one or more additional components of the patch 10 to the nonwoven layer 18. In such examples, the base layer 24 may comprise a relatively thin layer, wall, film, and/or other like barrier or piece of material extending between the first side 20 of the nonwoven layer 18 and one or more additional components of the patch 10 supported by and/or disposed on the first side 20. For example, the base layer 24 may assist in protecting one or more sensors, controllers, and/or other components of the patch 10 from contaminants, bodily fluids, infectious and/or contagious elements, wet conditions, and/or other potentially damaging or harmful environmental elements. In alternative embodiments, on the other hand, the base layer 24 may be omitted, and nonwoven layer 18 may be configured to assist in protecting the components of the patch 10 from such potentially damaging or harmful environmental elements.

The patch 10 may also include one or more flex circuit assemblies 26. In such embodiments, an example flex circuit assembly 26 may include, among other things, at least one substrate 28 having a component of the flex circuit assembly 26 disposed thereon, at least partially embedded therein, supported thereby, and/or otherwise connected thereto. For example, as shown in FIG. 1 a substrate 28 of the assembly 26 may include a first side 30 (e.g., a top) and a second side 32 (e.g., a bottom) disposed opposite the first side 30. The substrate 28 may be made from any of the materials described above with respect to the release liner 12 and the nonwoven layer 18. Additionally or alternatively, the substrate 28 may comprise a printed circuit board or other substantially rigid, substantially electrically insulative material. In such examples, the substrate 28 may be made from polyamide or other known materials (e.g., Kapton®) commonly used in manufacturing printed circuit boards.

The substrate 28 may include a first portion 33 comprising a relatively narrow strip of material, and the first portion 33 may at least partially define a longitudinal axis A of the substrate 28. For example, the longitudinal axis A of the substrate 28 may pass substantially centrally through the first portion 33. The first portion 33 may have any width, length, thickness, and/or other configuration and, in some examples, the width, length, and thickness of at least the first portion 33 (and/or of the substrate 28, generally) may be desirably minimized to reduce manufacturing costs. In example embodiments, the first portion 33 may have a width less than or equal to approximately 0.5 inches, and may have a length less than or equal to approximately 2.0 inches. In other embodiments, on the other hand, the first portion 33 may have a width greater than approximately 0.5 inches and/or a length greater than approximately 2.0 inches.

The patch 10 may also include at least one sensor configured to sense, detect, and/or otherwise determine a physiological parameter, a hemodynamic parameter, and/or other condition of the patient. In some examples, the patch 10 may include a plurality of sensors 34a, 34b, 34c, 34d (referred to collectively herein as "sensors 34"), and one or more of the sensors 34 may comprise a temperature sensor configured to determine a temperature of the patient, such as a temperature of a skin surface of the patient. The various sensors 34 of the patch 10 may be disposed at any location on or within the patch 10 convenient for assisting in determining one or more temperatures of the patch 10, of a skin surface of the patient on which the patch 10 is disposed, and/or of an ambient environment in which the patch 10 is being used. For example, one or more of the sensors 34 may be embedded substantially within the patch 10. In such embodiments, the one or more sensors 34 may be integral with the patch 10. Alternatively, the one or more sensors 34 may be substantially internal to the patch 10 such that the one or more sensors 34 may be positioned and/or otherwise configured to sense a temperature or other characteristic of at least part of the patch 10. In still further examples, one or more of the sensors 34 may be disposed proximate an outermost portion of the patch 10 and/or otherwise configured to determine an ambient temperature with minimal interference from heat emitted by the skin surface of the patient.

As shown in the example embodiment of FIG. 1, one or more of the sensors 34 may be connected to the substrate 28, and in some examples, at least the sensors 34a, 34d, 34b may be disposed on the first portion 33 of the substrate 28. Additionally, one or more of the sensors 34 may be disposed substantially along the longitudinal axis 34.

As shown in FIG. 1, the substrate 28 may also include a second portion 35 adjacent to and/or formed integrally with the first portion 33. The second portion 35 may have any configuration similar to and/or the same as the first portion 33. For example, the longitudinal axis A may extend through at least part of the second portion 35. Additionally, the second portion 35 may have any width, length, thickness, and/or other configuration and, in some examples, the width, length, and thickness of the second portion 35 may be desirably minimized to reduce manufacturing costs. In example embodiments, the second portion 35 may have a width less than or equal to approximately 0.5 inches, and may have a length less than or equal to approximately 2.0 inches. In other embodiments, on the other hand, the second portion 35 may have a width greater than approximately 0.5 inches and/or a length greater than approximately 2.0 inches.

As shown in FIG. 1, the width, length, and/or thickness of the second portion 35 may be the same as or different from the width, length, and thickness of the first portion 33. Further, at least one of the sensors 34 (e.g., sensor 34c) and/or various additional components of the flex circuit assembly 26 may be disposed on the second portion 35.

Although FIG. 1 illustrates an example embodiment of the patch 10 that includes four sensors 34, in other example embodiments, the patch 10 may include greater than or less than four sensors 34. For example, in some embodiments one or more of the sensors 34 illustrated in FIG. 1 may be omitted, while in other embodiments one or more additional sensors 34 may be included in the patch 10. In any of the example embodiments described herein, one or more of the sensors 34 may comprise a thermocouple, a thermistor, a thermometer, a resistance temperature detector (RTD), and/or any other like device useful in measuring temperature. In additional example embodiments, such sensors 34 may comprise any temperature sensitive material or coating known in the art. In additional example embodiments, the sensors 34 may be configured to sense, measure, and/or otherwise detect one or more additional properties, conditions, and/or characteristics of the patient on which the patch 10 is disposed. For example, in addition to temperature, one or more of the sensors 34 may be configured to detect heart rate, blood pressure, electrical current, and/or other parameters.

In any of the embodiments described herein, at least one of the sensors 34 (e.g., sensors 34a, 34d, 34b) may be substantially exposed to and/or disposed at least partly in contact with the skin surface of the patient while the second side 22 of the nonwoven layer 18 is in contact with the skin surface. Alternatively, in example embodiments in which the patch 10 includes the base layer 24 described above, the base layer 24 may overlay at least one of the sensors 34 (e.g., sensors 34a, 34d, 34b) and may space such sensors 34 from the skin surface. In such embodiments, the thermal resistance of the base layer 24 may be substantially negligible so as to maximize the accuracy of the one or more measurements made by the sensors 34. Alternatively, the thermal resistance of the base layer 24 may be known or empirically determined, and this thermal resistance may be taken into account when determining a temperature of the patient based on information received from one or more of the sensors 34.

As illustrated in FIG. 1, in example embodiments of the present disclosure the patch 10 may include a first sensor 34a connected to the substrate 28 and disposed within the first portion 26 along the longitudinal axis A. The patch 10 may also include a second sensor 34b connected to the substrate 28 and disposed within the first portion 26 along the longitudinal axis A. In such examples, the second sensor 34b may be spaced (e.g., longitudinally) from the first sensor 34a. The patch 10 may also include an additional sensor 34d connected to the substrate 28 and disposed within the first portion 26, along the longitudinal axis A, between the first and second sensors 34a, 34b. In such examples, the patch 10 may also include a further sensor 34c connected to the substrate 28 and disposed within the second portion 35. As will be described in greater detail below, in such examples the substrate 28 may be bent, folded, curved, and/or otherwise formed such that the second portion 35 overlays at least part of the first portion 33. In this way, the sensor 34c located within the second portion 35 may be disposed at a location substantially overlaying the sensor 34d. In further examples, the substrate 28 may be bent, folded, curved, and/or otherwise formed such that the sensor 34c located within the second portion 35 may be disposed at a location substantially overlaying the first sensor 34a or the second sensor 34b. Positioning and/or spacing the sensors 34 in this way may assist in determining the extent to which the thermal resistance of the various components of the patch 10 and/or ambient conditions affect the temperatures determined by the respective sensors 34. For instance, absolute temperatures determined by any of the sensors 34 described herein may be used to determine a core temperature of the patient based at least in part on a thermal resistance of at least one of the components of the patch and/or one or more correction factors associated therewith. Additionally or alternatively, differences between or averages of temperatures determined by any of the sensors 34 described herein may be used to determine a core temperature of the patient based at least in part on such thermal resistances and/or correction factors.

It is understood that the nonwoven layer 18, base layer 24, substrate 28, and/or other components of the patch 10 may have respective known thermal resistances, and such thermal resistances may depend upon, for example, the respective thicknesses of such components and/or the one or more materials utilized to form such components. For example, the thermal resistance of the plastics, rubber, polymers, fabrics, or other materials used to form such components of the patch 10 may be known in the art, and the core temperatures described herein may be determined based upon the known thermal resistances of such components. Additionally, as each of the components of the patch 10 may have different respective thicknesses, the thermal resistances of each component may be based on of the respective thicknesses.

With continued reference to FIG. 1, the patch 10 may also include at least one additional substrate supporting various components of the flex circuit assembly 26. For example, the patch 10 may include the substrate 28 described above (e.g., a first substrate) and at least one additional substrate 36 (e.g., a second substrate) disposed adjacent and/or connected to the substrate 28. In such examples, the second substrate 36 may be formed from any of the materials described above with respect to the first substrate 28, and/or may have a configuration substantially similar to the first substrate 28. For instance, the substrate 36 may include a first side 38 (e.g., a top) and a second side 40 (e.g., a bottom) disposed opposite the first side 38. In some examples, the substrate 36 may comprise a printed circuit board or other substantially rigid, substantially electrically insulative material. In such examples, the substrate 36 may be made from polyamide or other known materials (e.g., Kapton®) commonly used in manufacturing printed circuit boards. Alternatively, the substrate 36 may be made from a different material than the substrate 28. For example, the substrate 36 may be made from one or more relatively low-cost, substantially flexible plastics, polymers (e.g., polyethylene, polyester, etc.), or other materials in order to reduce the overall cost of manufacturing the patch 10.

The substrate 36 may have any width, length, diameter, thickness, shape, and/or other configuration and, in some examples, the width, length, diameter, thickness, and/or other configurations of the substrate 36 may be desirably minimized to reduce manufacturing costs. As shown in FIG. 1, an example substrate 36 may be substantially circular and/or substantially disc-shaped, and may be configured to support one or more components of the flex circuit assembly 26 on the first side 38 and/or on the second side 40. In example embodiments, the substrate 36 may have a diameter less than or equal to approximately 3.0 inches. In other embodiments, on the other hand, the substrate 36 may have a diameter greater than approximately 3.0 inches.

The patch 10 may also include at least one component configured to transmit and/or receive information associated with the temperatures determined by the respective sensors 34. For example, the patch 10 may include at least one antenna 42 configured to transmit and/or receive such information. Such an antenna 42 may comprise, for example, a coil of wire, a bead of aluminum, copper, and/or any other substantially conductive metal or alloy, screened conductive ink, or other substantially conductive material. As shown in FIG. 1, the antenna 42 may be connected to the substrate 36, and may be disposed on the first side 38 or on the second side 40. For example, the antenna 42 may be 2disposed on the first side (e.g., the top) of the substrate 36, each of the sensors 34 may be disposed on the first side (e.g., the top) of the substrate 28, and the substrates 28, 36 may be oriented such that the second side 40 (e.g., the bottom) of the substrate 36 faces at least part of the first side 30 of the substrate 28. In such examples, the second side 40 (e.g., the bottom) of the substrate 36 may face the first portion 33 of the substrate 28, and the first side (e.g., the top) of the substrate 36 may face the second portion 35 of the substrate 28.

Further, it is understood that in examples in which the antenna 42 comprises a bead of a substantially conductive metal or alloy, or a layer of conductive ink, the antenna 42 may be disposed on the substrate 36 through any known etching, screening, and/or other process. Any of the antennas 42 described herein may be connected to one or more components of the flex circuit assembly 26 and may be configured to transmit signals containing information indicative of the temperatures determined by the respective sensors 34. Additionally, as will be described in greater detail below, in some examples the patch 10 may include a single substrate. In such examples, the sensors 34, antenna 42 and/or other components of the flex circuit assembly 26 may be dispose on one or more surfaces of the single substrate. Further, as will be described in greater detail below, in further examples in which the patch 10 includes more than one substrate, any of the sensors 34, antennas 42, and/or other components of the flex circuit assembly 26 may be disposed on any of the substrates. Thus, it is understood that the patches 10 of the present disclosure are not limited to the example configuration illustrated in FIG. 1.

It is understood that in example embodiments in which the substrate 28 is bent, folded, curved, and/or otherwise formed such that the second portion 35 overlays at least part of the first portion 33, at least part of the substrate 28, such as at least part of the second portion 35, may be disposed between and/or may otherwise space the sensor 34c from the sensor 34d. In such embodiments, the second portion 35 of the substrate 28 may comprise a layer of electrically insulative material spacing and/or substantially electrically isolating the sensor 34c from the sensor 34d. Additionally or alternatively, the patch 10 may include a separate layer 44 of electrically and/or thermally insulative material spacing and/or substantially electrically isolating the sensor 34c from the sensor 34d.

The layer 44 of insulative material may be made from any of the materials described above with respect to the substrates 28, 36, and/or other components of the patch 10. Additionally or alternatively, the layer 44 may be made from a relatively thin electrically and/or thermally insulative foam material. Additionally, the layer 44 may have a shape, size, and/or configuration similar to at least the substrate 36. In some examples, the layer 44 may be disposed on, supported by, adhered to, and/or otherwise connected to the first side 38 of the substrate 36. Additionally, as noted above, the layer 44 may be disposed between, for example, the first side 38 of the substrate 36 and at least the part of the first side 32 of the substrate 28 forming the second portion 35. For instance, the layer 44 of electrically and/or thermally insulative material may include a first side 46 (e.g., a top) and a second side 48 (e.g., a bottom) disposed opposite the first side 46. In some examples, the second side 48 of the layer 44 may be disposed on the first side 38 of the substrate 36, and the first side 32 of the substrate 28 forming the second portion 35 may be disposed on the first side 46 of the layer 44.

The layer 44 may have any width, length, diameter, thickness, shape, and/or other configuration and, in some examples, the width, length, diameter, thickness, and/or other configurations of the layer 44 may be desirably minimized to reduce manufacturing costs. As shown in FIG. 1, an example layer 44 may be substantially circular and/or substantially disc-shaped, and may be shaped, sized, positioned and/or otherwise configured to substantially electrically isolate the sensor 34c and/or one or more components of the flex circuit assembly 26 from the antenna 42 and/or from the sensor 34d. In example embodiments, the layer 44 may have a diameter that is substantially similar to and/or the same as the diameter of the substrate 36 described above. Alternatively, the layer 44 may have a length, width, shape, size, and/or other configuration that is substantially similar to and/or the same as at least part of the second portion 35 of the substrate 28.

In some examples, the layer 44 of insulative material may be disposed on the first side 38 of the substrate 36, and may be positioned to overlay the sensors 34a, 34d, but not to overlay the second temperature sensor 34b described above. In such examples, the first portion 33 of the substrate 28 may extend beyond an outer diameter of the substrate 36 and/or of the layer 44, and the sensor 34b may be positioned on the first portion 33 such that the layer 44 of insulative material does not cover the sensor 34b.

Positioning the sensor 34b such that it is longitudinally or radially spaced from the outer diameter of the substrate 36 and/or from the outer diameter of the layer 44 may minimize the insulating effect of these components on the temperatures determined by the sensor 34b. For example, such spacing may minimize and/or substantially eliminate the effect that the thermal resistance of the substrate 36 and/or the layer 44 has on the temperatures determined by the sensor 34b. In such examples, longitudinally or radially spacing the sensor 34b from the outer diameter of the substrate 36 and/or from the outer diameter of the layer 44 may substantially thermally isolate the sensor 34b from such components.

Moreover, positioning the sensor 34b in this way may assist in determining if, and the extent to which, one or more of the additional sensors 34d, 34a, 34c are affected by the thermal resistance and/or other insulating effects of the substrate 36 and/or the layer 44. For example, as blood flows beneath and/or within the skin surface of the patient, a skin surface temperature determined by one or both of the sensors 34a, 34d may be greater than a corresponding skin surface temperature determined by the sensor 34b due at least in part to the thermal resistance of the substrate 36 and/or the layer 44 (e.g., the combination of these two components) being greater than the thermal resistance of the first portion 33 of the substrate 28, alone, on which the sensor 34 is disposed. In such examples, differences in skin surface temperatures determined by the sensor 34b and corresponding skin surface temperatures determined by the sensors 34d, 34a may be indicative of the accuracy and/or reliability of the skin surface temperatures determined by the sensors 34 of the patch 10. Accordingly, such differences may be utilized to determine the extent to which one or more temperatures determined by the respective sensors 34 should be modified or corrected, such as by a correction factor, when determining a corresponding temperature of the patient.

Further, positioning the sensor 34c such that it is spaced vertically or axially from, for example, the sensor 34d by the layer 44 of insulative material, the substrate 28, and/or the substrate 36 may assist in determining if, and the extent to which, one or more of the additional sensors 34d, 34a, 34b are affected by the thermal resistance and/or other insulating effects of such components. For example, as blood flows beneath and/or within the skin surface of the patient, respective skin surface temperatures determined by sensors 34d, 34a, 34b may be greater than a corresponding skin surface temperature determined by the sensor 34c due at least in part to the thermal resistances of the substrates 28, 36 and/or the layer 44 (e.g., the combination of these two components), and due to the relative exposure of the sensor 34c to ambient conditions. In such examples, differences in skin surface temperatures determined by the sensor 34c and corresponding skin surface temperatures determined by the sensors 34d, 34a, 34b may be indicative of the accuracy and/or reliability of the skin surface temperatures determined by the sensors 34 of the patch 10. Accordingly, such differences may also be utilized to determine the extent to which one or more temperatures determined by the respective sensors 34 should be modified or corrected, such as by a correction factor, when determining a corresponding temperature of the patient.

In example embodiments, the patch 10 may also include a cover layer 50 adhered and/or otherwise connected to the first surface 46 of the layer 44 of insulative material. As the second portion 35 of the substrate 28 may overlay at least part of the first surface 46 of the layer 44, the cover layer 50 may also be connected to the part of the second side 32 of the substrate 28 forming the second portion 35. In such examples, the cover layer 50 may overlay the temperature sensor 34c and the part of the second side 32 of the substrate 28 forming the second portion 35.

In example embodiments, the cover layer 50 may be made from any of the materials described above with respect to the substrates 28, 36, the release liner 12, and/or other components of the patch 10. Additionally, the cover layer 50 may have a shape, size, and/or configuration similar to at least the substrate 36 and/or similar to the layer 44. For instance, the cover layer 50 may include a first side 52 (e.g., a top) and a second side 54 (e.g., a bottom) disposed opposite the first side 52. In some examples, the second side 54 of the cover layer 50 may be disposed on and/or connected to the first side 46 of the layer 44. The second side 54 of the cover layer 50 may also be disposed on and/or connected to the part of the second side 32 of the substrate 28 forming the first portion 33.

The cover layer 50 may have any width, length, diameter, thickness, shape, and/or other configuration and, in some examples, the width, length, diameter, thickness, and/or other configurations of the layer 44 may be substantially similar to and/or the same as the corresponding configurations of the layer 44. Additionally, the cover layer 50 may include one or more visual indicia 56 configured to assist in positioning the patch 10 on a skin surface of a patient. For example, the visual indicia 56 may comprise one or more lines, arrows, or other markings disposed at a location on the cover layer 50 that is easily visible by a healthcare professional when removably attaching the patch 10 to the skin surface. In example embodiments, one or more such visual indicia 56 may be located on the first surface 52, and the visual indicia 56 may indicate a preferred orientation of the patch 10 relative to a blood vessel of the patient located below the skin surface. For example, the visual indicia 56 may be aligned with and/or may extend substantially parallel to the longitudinal axis A of the substrate 28. In such examples, the visual indicia 56 may be aligned with and/or may extend substantially parallel to each of the sensors 34 connected to the substrate 28. As a result, orienting the patch 10 on the skin surface of the patient such that the visual indicia 56 is aligned with and/or extends substantially parallel to a blood vessel of the patient will ensure that the sensors 34 are also aligned with and/or disposed along a line/axis that extends substantially parallel to the blood vessel. Orienting the patch 10 in this way will ensure that the sensors 34 are disposed as close as possible to the blood vessel, and as a result, will maximize the accuracy of the temperature determinations made by the respective sensors 34.

Figure 2:
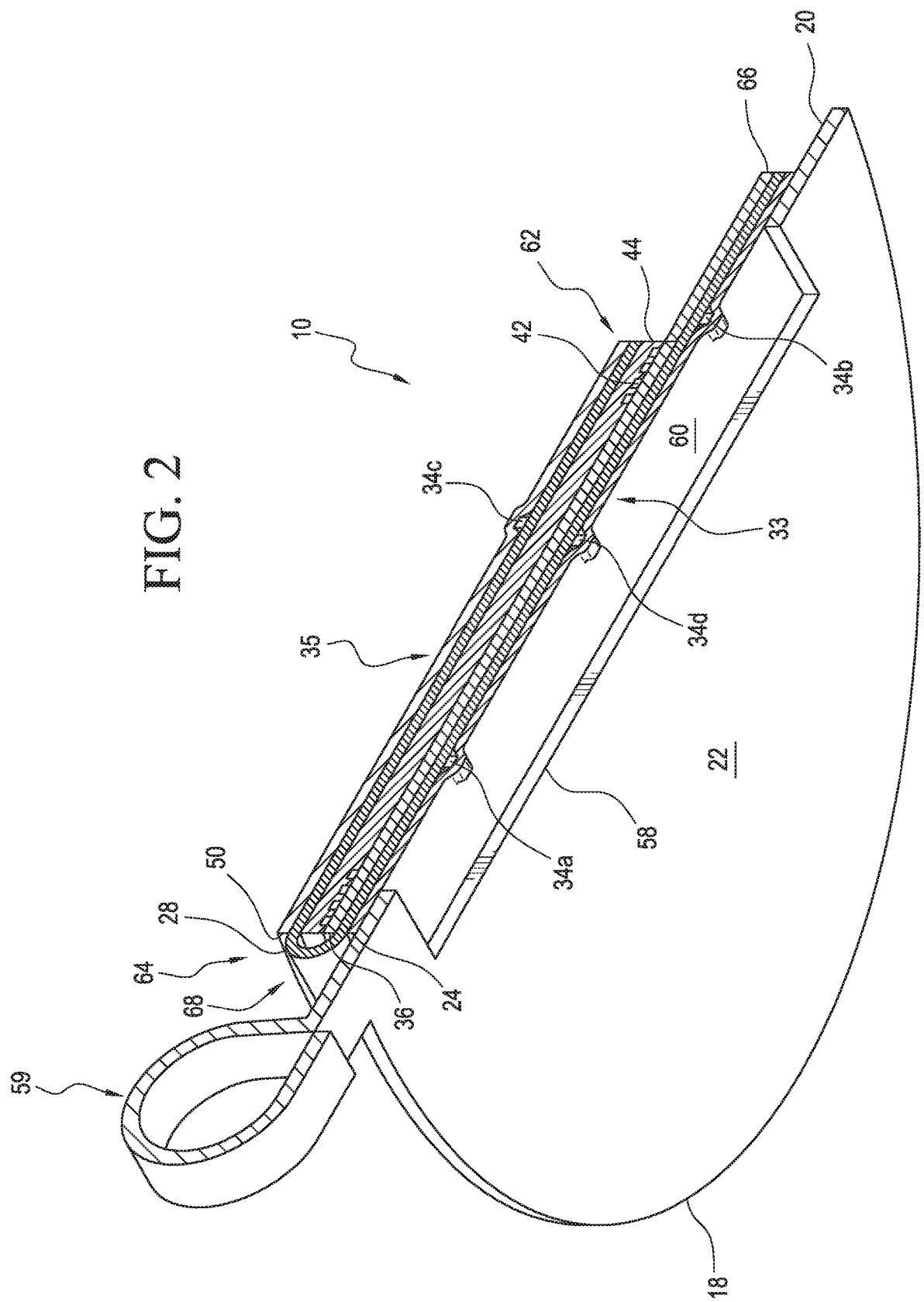
FIG. 2 illustrates a cross-sectional view of the patch shown in FIG. 1.

FIG. 2 illustrates an example cross-section of the patch 10 including the various components described above with respect to FIG. 1. As shown in in FIG. 2, in some examples the nonwoven layer 18 may include an opening 58 extending from the first side 20 of the nonwoven layer 18 to the second side 22. The nonwoven layer 18 may also include a grip 59 extending proximal to the opening 58, the substrates 28, 36, and/or other components of the patch 10.

In such examples, the opening 58 may extend substantially along at least a portion of the longitudinal axis A (FIG. 1) of the substrate 28, and may be configured such that one or more of the sensors 34 may be disposed in relatively close proximity to (e.g., substantially adjacent to and/or substantially contacting) the skin surface of the patient on which the patch 10 is disposed. For example, the substrate 28 may be positioned relative to the opening 58 such that one or more of the sensors 34a, 34d, 34b are facing and/or substantially overlaying the opening 68. As a result, in examples in which the base layer 24 has been omitted, the one or more of the sensors 34a, 34d, 34b may be disposed substantially adjacent to and/or substantially in contact with the skin surface of the patient when the patch 10 is disposed thereon. In some examples in which the base layer 24 has been omitted, the one or more of the sensors 34a, 34d, 34b may be disposed in actual contact with the skin surface of the patient when the patch 10 is disposed thereon. Alternatively, in embodiments in which the patch 10 includes the nonpermeable base layer 24 described above, the opening 58 may allow for at least a portion of a bottom surface 60 of the base layer 24 to be disposed substantially adjacent to, substantially in contact with, or in actual contact with the skin surface. In such examples, the one or more of the sensors 34a, 34d, 34b may be spaced from the skin surface by a thickness of the base layer 24.

The grip 59 may be configured to assist a healthcare professional with positioning the patch 10 on the skin surface of the patient and/or removing the patch 10 therefrom. For example the biocompatible adhesive disposed on the second side 22 of the nonwoven layer 18 may be prone to sticking to the healthcare professional's fingers once the release liner 12 (FIG. 1) has been removed. Additionally, the adhesive may make removal of the patch 10 from the skin surface of the patient difficult and potentially painful for the patient. To overcome these difficulties, the portion of the second surface 22 forming the grip 59 may be free from the biocompatible adhesive described above such that the healthcare professional may grasp the grip 59 without the patch 10 sticking to the professional's fingers. Additionally, since no adhesive is disposed on the grip 59, the portion of the second surface 22 forming the grip 59 may not be adhered to the skin surface of the patient when the patch 10 is removably attached thereto. As a result, the grip 59 may provide the healthcare professional with a region of the patch 10 to grasp when removing the patch 10 from the skin surface. In some examples, at least part of the nonwoven layer 18 may be looped and/or folded onto itself at the grip 59 to provide additional rigidity and/or surface area for grasping.

As noted above, the layer 44 of insulative material may be disposed on the first side 38 of the substrate 36, and may be positioned to overlay the sensors 34a, 34d, but not to overlay the second temperature sensor 34b described above. This configuration is illustrated in FIG. 2. In particular, as shown in FIG. 2 a distal portion 62 of the layer 44 of insulative material overlays a corresponding portion of the antenna 42 and a distal portion of the substrate 36. Similarly, a proximal portion 64 of the layer 44 overlays a corresponding portion of the antenna 42 and a proximal portion of the substrate 36. The distal portion 62 of the layer 44 does not, however, cover and/or otherwise overlay the distal sensor 34b. Thus, while the layer 44 may substantially thermally isolate the sensors 34a, 34d from ambient influences, such influences may have a relatively greater effect on temperature determinations made by the distal sensor 34b. In some examples, the patch 10 may also include an additional layer 66 of nonwoven material overlaying the distal sensor 34b. The layer 66 of nonwoven material may be substantialy similar to and/or the same as the nonwoven layer 18, and may provide a minimial level of thermal insulation to the sensor 34b. The additional layer 66 of nonwoven material overlaying the distal sensor 34b may also provide at least some protection from sweat, blood, bodily fluids, and/or other contaminants. It is understood that because the layer 66 of nonwoven material has a known thermal resistance, temperature determinations made using the sensor 34b may be corrected and/or otherwise modified based at least in part on such a known thermal resistance.

Additionally, as noted above the substrate 28 may include a first portion 33 on which one or more of the sensors 34a, 34d, 34b are disposed, and a second portion 35 on which the sensor 34c is disposed. As shown in at least FIGS. 2, 3, and 4, the first portion 33 may extend along the second side 40 (e.g., the bottom) of the substrate 36, and the second portion 35 may be disposed opposite the first portion 33. In such examples, the substrate 28 may also include a folded portion 68 disposed between the first portion 33 and the second portion 35. In such examples, the folded portion 68 may comprise a bent, curved, and/or otherwise folded section of the substrate 28 that is configured to position the second portion 35 such that the sensor 34c substantially overlays the sensor 34d. Additionally, as shown in at least FIG. 2 the folded portion 68 may be configured to permit the layer 44 to be disposed between, for example the first side 38 of the substrate 36 and the part of the first side 30 of the substrate 28 forming the second portion 35.

Figure 3:
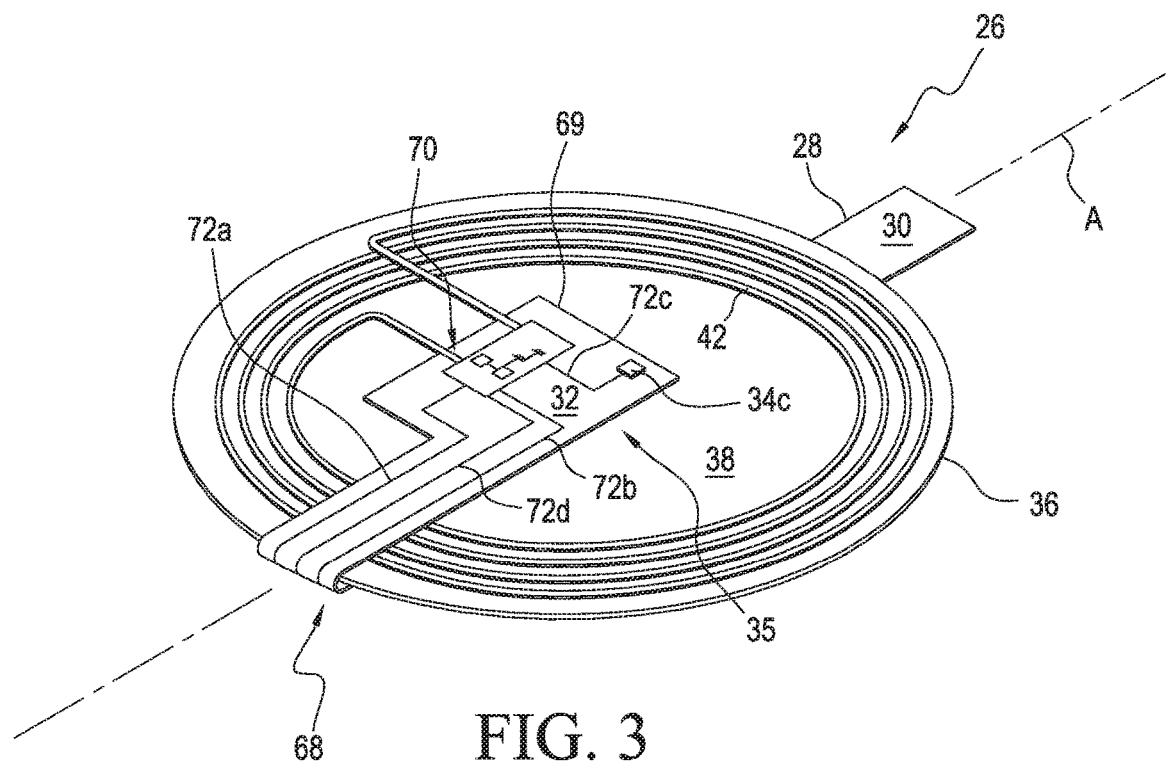
FIG. 3 illustrates a top view of components of the patch shown in FIG. 1.
Figure 4:
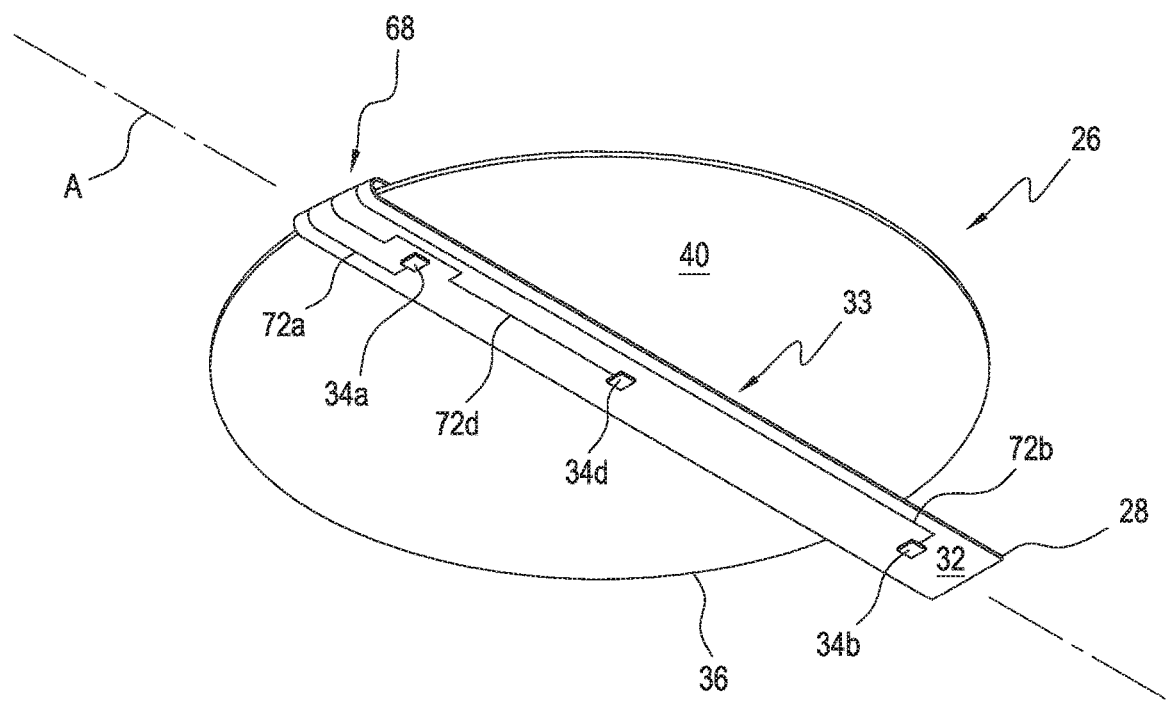
FIG. 4 illustrates a bottom view of components of the patch shown in FIG. 1.

FIGS. 3 and 4 illustrate the substrates 28, 36 described above with respect to FIGS. 1 and 2. The layer 44 has been omitted from FIGS. 3 and 4 for clarity. As shown in FIGS. 3 and 4, an example patch 10 of the present disclosure may also include a circuit 69 disposed on the second side 32 of the substrate 28. For example, the circuit 69 may be connected to the part of the second side 32 forming the second portion 35, and the circuit 69 may include a plurality of components 70 configured to assist in receiving, transmitting, and/or processing signals received from the sensors 34. In example embodiments, such components 70 may include one or more microprocessors, filters, amplifiers, resistors, transistors, and/or other electronic components typically associated with known sensor control circuits. In such examples, each of the respective sensors 34 may be connected to one or more of the components 70 via respective leads 72a, 72b, 72c, 72d (referred to collectively herein as "leads 72") disposed on the second surface 32 of the substrate 28. Such leads 72 may comprise beads of copper, aluminum, and/or any other substantially electrically conductive metal or alloy connected to the substrate 28. Further, as illustrated in at least FIGS. 3 and 4, the antenna 42 may be connected to one or more components 70 of the circuit 69. In such examples, one or more leads may connect the antenna 42 to such components 70. As noted above, in some examples, the patch 10 may include one or more reference resistors. In such examples, one or more of the components 70 may comprise a reference resistor having a known resistance value. In such examples, one or more of the temperature sensors 34 may use a differential reading across the reference resistor to compensate for variations in, for example, power delivered to the circuit 69.

Figure 5C:
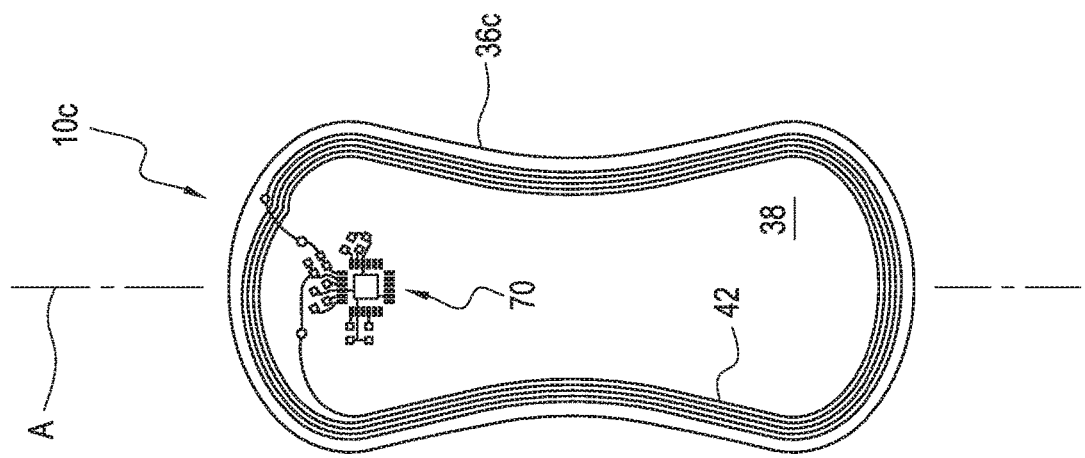
FIG. 5c illustrates a top view of components of an example patch according to a further embodiment of the present disclosure.
Figure 5B:
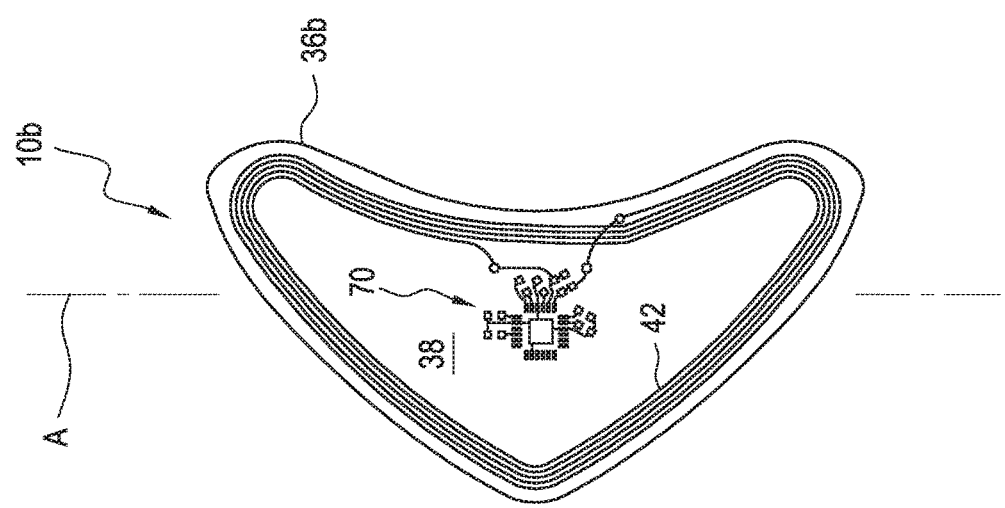
FIG. 5b illustrates a top view of components of an example patch according to another embodiment of the present disclosure.
Figure 5A:
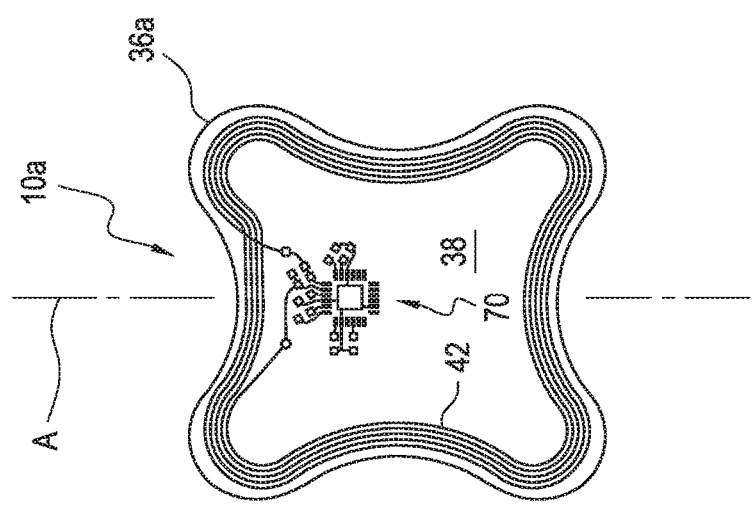
FIG. 5a illustrates a top view of components of an example patch according to an embodiment of the present disclosure.

In the examples described above with respect to FIGS. 1-4, the patch 10 and/or the substrate 36 is illustrated as having a substantially circular and/or substantially disc-shaped configuration. In other examples, however, the patch 10 and one or more of its components may have any other shape, size, or configuration known in the art. Various additional example configurations of the patch 10 are illustrated in FIGS. 5a-5c. In particular, FIG. 5a illustrates an example patch 10a with a substrate 36a having a substantially rectangular, substantially star-shaped configuration. FIG. 5b illustrates an example patch 10b with a substrate 36b having a substantially triangular, substantially boomerang shape. FIG. 5c illustrates an example patch 10c with a substrate 36c having an elongated substantially bean-shaped or substantially elongated configuration. The various shapes, sizes, orientations, and/or other configurations of the example patches 10a, 10b, 10c illustrated in FIGS. 5a-5c may improve patient comfort, ease of placement of the patches 10a, 10b, 10c on a respective skin surface of the patient, and durability of the patches 10a, 10b, 10c. Such configurations may result in improved signal fidelity, improved temperature measurement accuracy, and/or other performance improvements over the period of time in which the respective patches 10a, 10b, 10c are worn by the patient.

Figure 6:
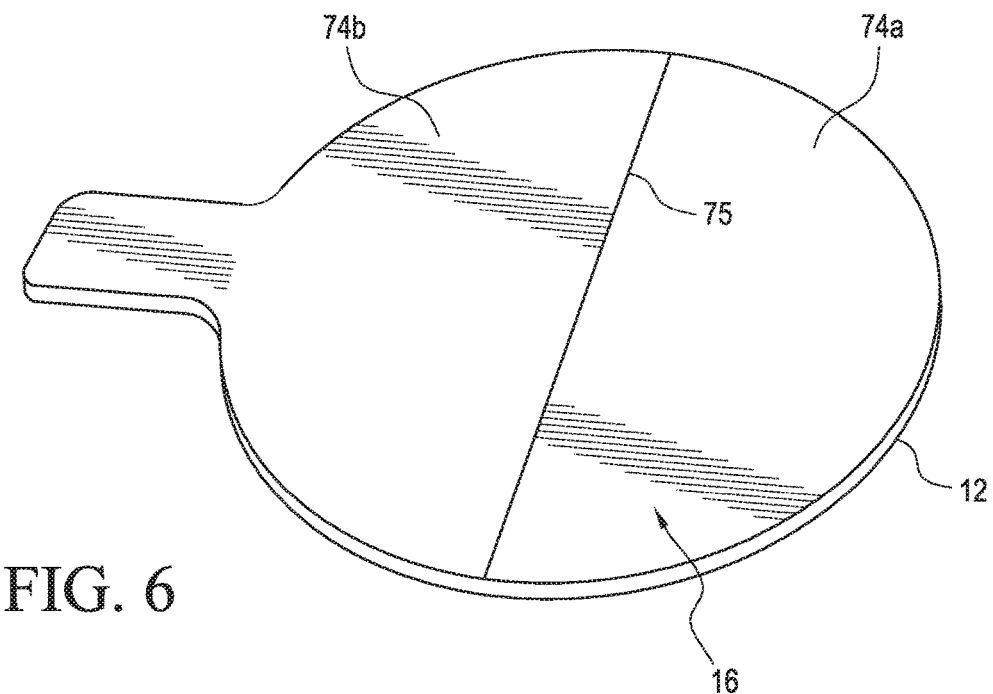
FIG. 6 illustrates an example releasable patch liner according to an embodiment of the present disclosure.

FIG. 6 illustrates the release liner 12 described above with respect to FIG. 1, and FIG. 7 illustrates the second side 22 of the nonwoven layer 18. As shown in FIG. 6, the release liner 12 may comprise first and second halves 74a, 74b separated by a seam 75. The seam 57 may comprise a score line, perforations, and/or a cut in the release liner 12. In such examples, one of the halves (e.g., the second half 74b) may be removed from the nonwoven layer 18 before the remaining half (e.g., the first half 74a) is removed. Such a configuration may assist in removing the release liner 12 from the nonwoven layer 18.

Figure 7:
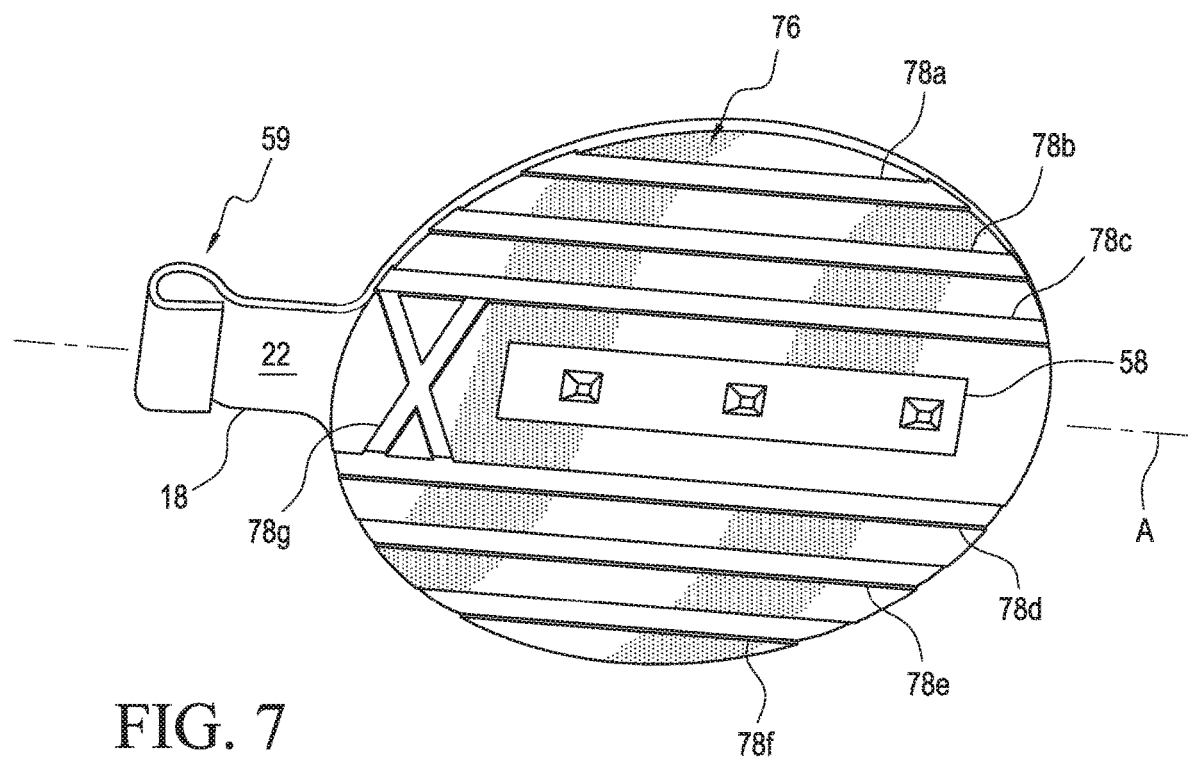
FIG. 7 illustrates a bottom view of the patch shown in FIG. 1 with the release liner removed.

Further, as shown in FIG. 7, to assist with removably attaching the patch 10 to a skin surface of the patient, any known biocompatible adhesive 76 may be disposed on at least a portion of the second side 22 of the nonwoven layer 18. Alternatively, one or more elastic straps, bands, belts, ties, or the like may be connected to at least a portion of the patch 10 to assist in removably attaching the patch 10 to the skin surface of the patient. With reference to the embodiment of FIG. 7, in some examples the second side 22 of the nonwoven layer 18 may include a plurality of strips, channels, substantially planar surfaces, grooves, and/or other areas 78a-78g (referred to collectively herein as "areas 78") in which substantially none of the adhesive 76 is disposed. For example, during manufacturing of the nonwoven layer 18, the areas 78 may be covered with a removable material when the adhesive 76 is disposed on the second side 22 such that substantially no adhesive 76 is disposed on the areas 78. Alternatively, in further embodiments the adhesive 76 may be applied to substantially the entire second side 22, and such adhesive 76 may be subsequently removed at the areas 78. In still further embodiments, a non-adhesive web (not shown) may be attached to the second side 22 of the nonwoven layer 18, and may cover at least some of the adhesive 76. In such examples, the web may form one or more of the areas 78.

In any of the examples described herein, the areas 78 may result in a patch 10 having varying adhesive strength. When, for example, the grip 59 is pulled in the plane defined by the second side 22 on which the adhesive 76 is disposed, such areas 78 may enable the patch 10 to stretch, buckle, and/or otherwise at least partially deform. Such deforming of the patch 10 may increase patient comfort when the patch 10 is removed from the skin surface of the patient.

Figure 8:
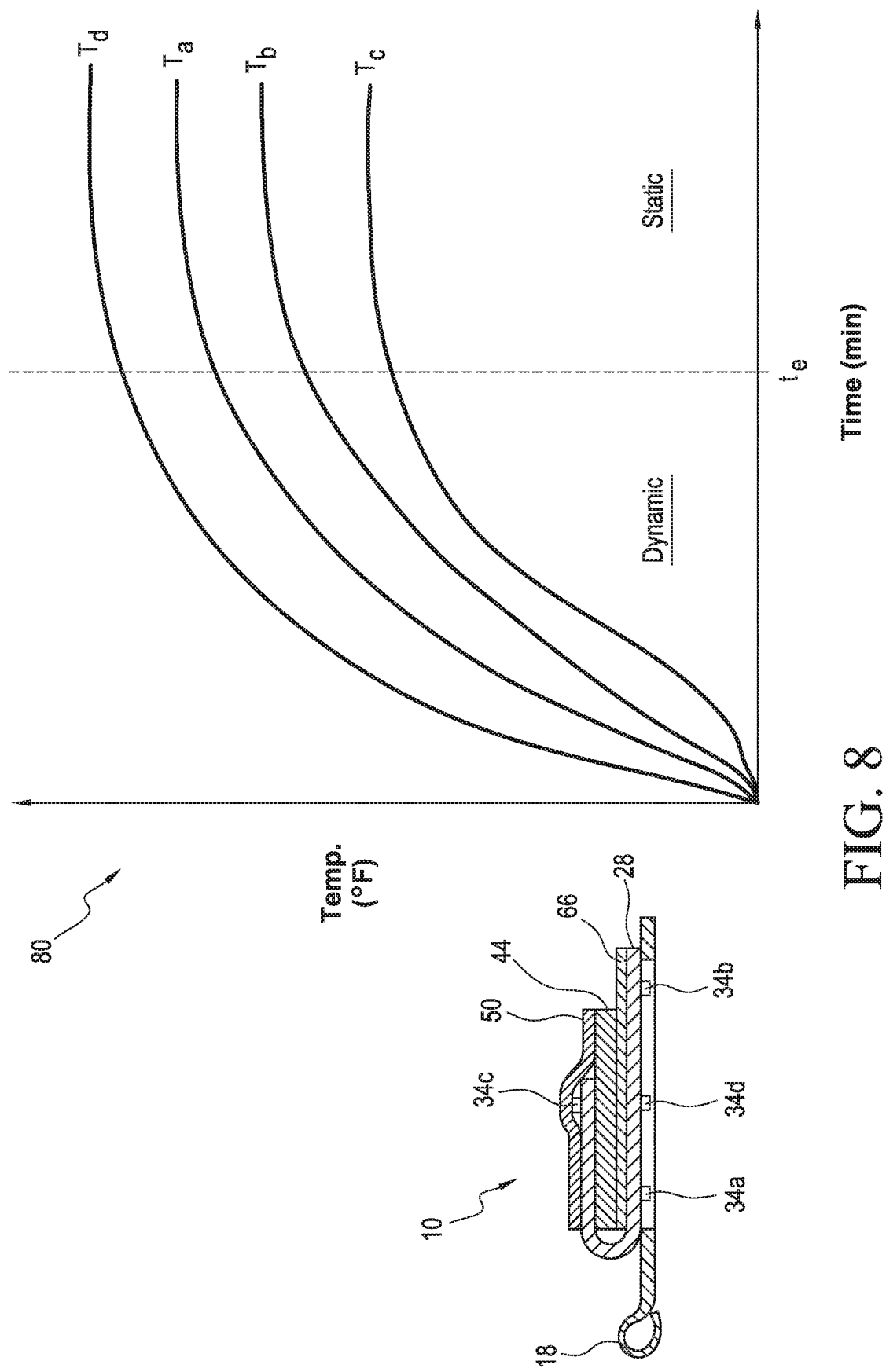
FIG. 8 illustrates a cross-sectional view of an example patch, and a temperature vs. time graph associated with the example patch.
Figure 8A:
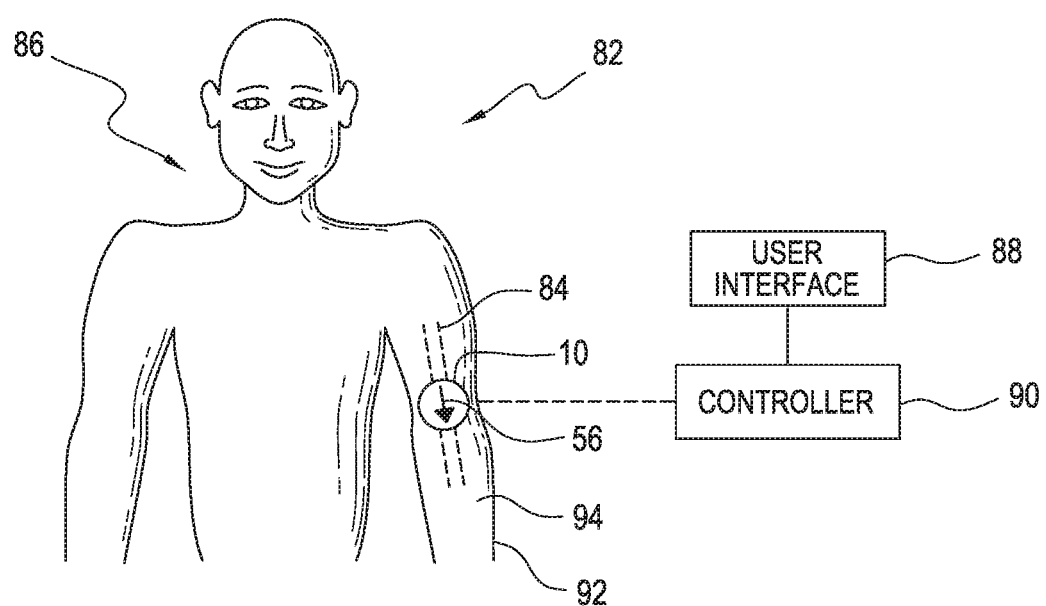
FIG. 8a illustrates an example patch disposed on a skin surface of a patient according to an example embodiment of the present disclosure.

FIG. 8 illustrates a cross-section of the example patch 10 described above, along with a temperature vs. time graph 80 associated with patient temperature determinations made by the respective sensors 34 included in the patch 10 of FIG. 8. Further, FIG. 8a illustrates an example system 82 of the present disclosure including the patch 10. With reference to FIG. 8a, the system 82 may, for example, comprise a patient monitoring system, a temperature determination system, and/or any other system configured to monitor a patient and, in some embodiments, to determine a temperature and/or a hemodynamic parameter of the patient.

As shown in FIG. 8a, an example system 82 may include one or more patches 10 and/or other temperature measurement devices configured to be disposed proximate a vessel 84 of a patient 86 such as an artery, vein, capillary, or other type of blood vessel. Such patients 86 may be, for example, human beings in need of medical treatment or diagnosis, and in some examples, the patient 86 may receive care from a healthcare professional. The system 82 may also include a user interface 88 operably connected to the patch 10 and/or a controller 90 operably connected to at least one of the patch 10 and the user interface 88.

The patch 10 may be removably connected, attached, affixed, disposed on, adhered, and/or otherwise connected to a limb 92 of the patient 86. For example, the patch 10 may be temporarily connected to and/or may temporarily contact at least a portion of an arm, a leg, or other limb 92 during use. In particular, the patch 10 may be disposed on and/or removably attached to a skin surface 94 of the limb 92. Alternatively, the patch 10 may be temporarily connected to and/or may temporarily contact the forehead, the clavicle, and/or any other body part or corresponding skin surface 94 of the patient 86 during use. Accordingly, the patch 10 may be removably attached to any skin surface 94 of the subject, and removably attaching the patch 10 to any of the skin surfaces 94 described herein may assist in the determination of a core temperature and/or any other like internal body temperature of the patient 86. As noted above, the visual indicia 56 included on the cover layer 50 of the patch 10 may indicate a preferred orientation of the patch 10 relative to a blood vessel of the patient, and as shown in FIG. 8a, in some examples the patch 10 may be positioned on the skin surface 94 of the patient 86 such that the visual indicia 65 extends substantially parallel and/or otherwise aligned with the blood vessel 84 of the patient 86 located within the limb 92 of the patient 86 on which the patch 10 is disposed.

The user interface 88 may include one or more buttons, switches, keypads, dials, knobs, and/or other like devices configured to assist in controlling one or more functions of the patch 10, the various controllers and/or other components 70 of the circuit 69, and/or the controller 90. Such user interfaces 16 may be useful in, for example, energizing and/or deenergizing one or more components 70 of the patch 10, activating and/or deactivating one or more of the temperature sensors 34, toggling through and/or selecting one or more modes of operation or display, enabling and/or disabling one or more alarms or signals associated with patch operation, initiating a single instantaneous patient temperature determination, initiating a substantially continuous and/or repeating patient temperature determinations, and/or other like modes, functions, or operations. In some examples, the system 82 may include one or more RFID readers or other like reader devices (not shown) configured to communicate and/or interact with the antenna 42, the components 70, and/or other components of the patch 10. In such examples, the user interface 88 and/or the controller 90 may be components of the RFID reader.

Additionally, the user interface 88 may include a liquid crystal diode (LCD) screen, a light emitting diode (LED) display, a digital read-out, and/or any other like display device. Such a display device of the user interface 88 may be configured to, for example, indicate and/or otherwise output the determined temperature of the patient 86 during operation of the patch 10. The user interface 88 may be configured to display the temperature substantially instantaneously and/or substantially continuously depending on the mode of operation of the patch 10 and/or of the controller 90. The display device of the user interface 88 may be, for example, a substantially numerical digital display, and may also be configured to display any other typical operating information such as, for example, individual temperature determinations made by the respective sensors 34, a temperature vs. time trend line, a temperature vs. time plot 80 as illustrated in FIG. 8, and/or any other graphical depiction.

The controller 90 may be configured to control the operation of each component of the patch 10 and/or of the user interface 88. In some embodiments, the controller 90 may comprise one or more processors, memory components, I/O devices, wired and/or wireless communication devices, and/or other computer, server, and/or electronic computing device components known in the art. In an example embodiment, the controller 90 may be configured to receive signals, information, measurements, and/or other data from the one or more sensors 34 of the patch 10, and to calculate and/or otherwise determine a temperature of the patient 86 (e.g., a core temperature) based at least in part on the information received. In any of the examples described herein, the controller 90 may include, may be connected to, and/or may be in communication with a hard drive, a memory stick, an SD card, a removable memory device, network and/or cloud-based memory, and/or any other computer-readable storage device (not shown). Such a computer-readable storage device may include instructions stored thereon that, when executed by a controller 90, cause the controller 90 to perform various operations, including any of the steps, processes, determinations, calculations, selections, and/or other operations described herein.

The controller 90 may also be configured to execute one or more commands and/or control programs. Such commands and/or control programs may include and/or may comprise the instructions described above, and may be stored on the computer-readable storage device. For example, the controller 90 may be programmed to initiate one or more alarms in response to determining a patient temperature that is greater than or equal to a predetermined threshold temperature. In addition, the controller 90 may be configured to initiate such an alarm during a substantially continuous patient temperature calculation operation if the calculated patient temperature increases and/or decreases at a rate that is greater than or equal to a predetermined threshold temperature change rate. In such an embodiment, the controller 90 may substantially continuously calculate a patient temperature change rate, and the threshold temperature and/or the threshold temperature change rate may be indicative of the onset of infection and/or of a decline in the health of the patient 86. In an example embodiment, such a threshold temperature may be approximately 100° F. and such a threshold change rate may be approximately 0.02° F./minute. In additional examples, the threshold temperature and/or the threshold change rate may be greater than or less than the example temperature and change rate noted above. The controller 90 may also initiate such an alarm to indicate that a location and/or orientation of the patch 10 should be changed, and such a location and/or orientation change alarm may be initiated in response to one or more sensed metrics indicative of blood flow beneath the skin surface 94. Such metrics may include, for example, various skin surface temperatures measured by the respective sensors 34 of the patch 10.

The patch 10 may also include one or more additional components not illustrated in FIG. 8*a*. For example, in some embodiments the patch 10 may include one or more lights, LEDs, speakers, sirens, and/or other like devices configured to emit an audible and/or optical alarm or signal in response to a command or signal from the controller 90. As described above, such an alarm or other signal may be initiated by, for example, the controller 90 when a patient temperature meets or exceeds a threshold temperature. In additional example embodiments, such an alarm or signal may be initiated during a substantially continuous temperature determination operation where the rate of patient temperature change meets or exceeds the predetermined patient temperature change rate threshold.

Additionally, the patch 10 may include one or more transponders, transceivers, or other components configured to receive signals, power, or information from a remote source, such as a remote controller 90 or the like. Such components of the patch 10 may also include one or more devices configured to transmit signals, data, and/or other information to remote receivers. For example, an example transponder may be configured to transmit information corresponding to one or more sensed temperatures to a remote computer, controller 90, or other like device utilized in the calculation of core temperatures of the patient 86. Such an example transponder may facilitate communication with remote devices using, for example, radio, infrared, wireless, WI-FI®, BLUETOOTH®, ZIGBEE® near field communication, and/or other technologies. Accordingly, such a transponder may enable monitoring of patients 86 fitted with the patch 10 from one or more remote locations within, for example, a hospital or other healthcare facility. In addition, such a transponder may facilitate a wireless internet connection with one or more routers, servers, or the like. Further, although not shown in FIG. 8*a*, it is understood that example patches 10 may also include one or more USB ports, communication terminals, or other like components configured to facilitate connecting the patch 10 to one or more computers, controllers 90, user interfaces 88, monitors, servers, routers, or other like monitoring devices via one or more cables, wires, leads, or other like connection devices.

With reference to FIG. 8, it is understood that once the patch 10 is removably attached to the skin surface 94 of the patient 86, the temperatures determined by the various sensors 34 may increase until the patch 10 and/or its components reach an equilibrium condition. For example, when the patch 10 is initially disposed on the skin surface 94, the actual temperature of the patch 10, the sensors 34, the nonwoven layer 18, and/or other components of the patch 10 may increase due to heat being conducted from the skin surface 94 to the patch 10. Similarly, when the patch 10 is initially disposed on the skin surface, the skin surface temperatures determined by the respective sensors 34 of the patch 10 may also increase (although the actual temperature of the skin surface 94 may remain substantially constant). This increase in the initial skin surface temperatures determined by the respective sensors 34*a*, 34*b*, 34*c*, 34*d* is represented by the corresponding temperature curves Ta, Tb, Tc, Td in the "Dynamic" portion of the temperature vs. time graph 80. For example, the temperature curve Ta corresponds to skin surface temperatures measured and/or otherwise determined by the sensor 34*a*, the temperature curve Tb corresponds to skin surface temperatures measured and/or otherwise determined by the sensor 34*b*, the temperature curve Tc corresponds to skin surface temperatures measured and/or otherwise determined by the sensor 34*c*, and the temperature curve Td corresponds to skin surface temperatures measured and/or otherwise determined by the sensor 34*d*.

As the temperature of the patch 10 rises and approaches the actual temperature of the skin surface 94, the patch 10 may reach an equilibrium condition identified on the temperature vs. time graph 80 at time $t_e$. At time $t_e$ the temperature of the patch 10 and at least some of its components may be approximately equal to the actual temperature of the skin surface 94 on which the patch 10 is disposed. As a result, beyond the time $t_e$ the skin surface temperatures determined by the respective sensors 34 of the patch 10 may remain relatively constant (in situations in which the temperature of the skin surface 94 may remains substantially constant). Such relatively and/or substantially constant skin surface temperatures determined by the respective sensors 34*a*, 34*b*, 34*c*, 34*d* are represented by the corresponding temperature curves Ta, Tb, Tc, Td in the "Static" portion of the temperature vs. time graph 80.

It is understood that the temperatures determined by the respective sensors 34 may be more reliable during the Static condition represented in the graph 80 (i.e., after the time $t_e$ has elapsed since disposing the patch 10 on the skin surface 94) than during the Dynamic condition. Accordingly, in some examples a patient temperature, such as a core temperature of the patient, may be determined by determining that the patch 10 has been disposed on the skin surface 94 for at least a predetermined period of time (e.g., a period of time greater than or equal to the time $t_e$), and determining first, second, third, and/or fourth skin surface temperatures with the respective sensors 34*a*, 34*b*, 34*c*, 34*d* after the predetermined period of time has elapsed. In such examples, a timer and/or other component 70 of either the patch 10 or the controller 90 may assist in making such determinations. Additionally, in such examples one or more components 70 of the patch 10 and/or the controller 90 may use one or more of the first, second, third, and/or fourth skin surface temperatures determined by the respective sensors 34a, 34b, 34c, 34d as inputs into a patient temperature (e.g., a core temperature) algorithm to determine the temperature of the patient.

With continued reference to FIG. 8, it is understood that the sensor 34c is the sensor most directly exposed to conditions of an ambient environment, while the sensors 34a, 34b are substantially thermally isolated (e.g., substantially insulated) from the ambient condition by the substrate 28, the layer 44, and the cover layer 50. In such embodiments, conditions of the ambient environment (e.g., an ambient temperature) may have a larger effect on temperature determinations made the sensor 34c than on corresponding temperature determinations made by one or both of the sensors 34a, 34d. Additionally, while the sensors 34a, 34b may be substantially thermally isolated (e.g., substantially insulated) from ambient conditions by the substrate 28, the layer 44, and the cover layer 50, only the substrate 28 and the layer 66 of nonwoven material may insulate the sensor 34b from such conditions. Because the combination of the substrate 28, the layer 44, and the cover layer 50 may have a (combined) thermal resistance that is greater than the (combined) thermal resistance of the substrate 28 and the layer 66, conditions of the ambient environment (e.g., an ambient temperature) may have a larger effect on skin surface temperature determinations made by the sensor 34b than on corresponding determinations made by one or both of the sensors 34a, 34d.

The differences in the corresponding temperatures determined by the respective sensors are represented by the spacing and position of the temperature curves Ta, Tb, Tc, Td shown in the graph 80. In particular, for a given (substantially constant) actual skin surface temperature above ambient temperatures, it is understood that the temperature determined by the sensor 34d may be greater than or substantially equal to the temperature determined by the sensor 34a, that the temperature determined by the sensor 34a will be greater than the temperature determined by the sensor 34b, and that the temperature determined by the sensor 34b will be greater than the temperature determined by the sensor 34c. In example embodiments of the present disclosure, the differences between the corresponding temperatures determined by the respective sensors 34 may be used to determine a multiplier, a weight, and/or any other correction factor, and such a correction factor may be used by the controller 90 and/or by components 70 of the patch 10 when determining a temperature of the patient 86. Additionally or alternatively, in any of the examples described herein the thermal resistance of at least one of the substrate 28, the layer 44, the cover layer 60, the layer 66 of nonwoven material, and/or other components of the patch 10 may also be used as an input in determining the correction factor.

Further, based at least in part on normal variations in the thermal resistance of a skin layer corresponding to the skin surface 94, skin surface temperatures determined by the sensors respective sensors 34 may vary. These variations in the thermal resistance of such a skin layer may be caused by changes in ambient conditions and/or by physical activity, health, illness, disease state, or other physical conditions of the patient 86. For example, subjecting the skin layer to a decrease in ambient temperature may result in corresponding increase in thermal resistance of the skin layer caused by closing of capillaries and/or other blood vessels. Alternatively, subjecting the skin layer to an increase in ambient temperature may result in a corresponding decrease in thermal resistance of the skin layer caused by opening of capillaries and/or other blood vessels. In example embodiments of the present disclosure, the variable or otherwise dynamic thermal resistance of the skin layer on which the patch 10 is disposed may determine the degree to which temperatures determined by the sensors 34 should be adjusted or corrected, such as by a multiplier, a weight, and/or by another correction factor, when determining a temperature of the patient 86. Alternatively, the variable thermal resistance of the skin layer may determine the degree to which the temperature of the patient 86 (e.g., a core temperature) should be adjusted or corrected.

FIGS. 9-14 illustrate further example patches of the present disclosure. Although not illustrated in FIGS. 9-14, it is understood that such example patches may also include the release liner 12, nonwoven layer 18, base layer 24, layer 44 of insulative material, cover layer 50, and/or any of the other components described above with respect to the patches 10 shown in FIGS. 1-8a. Additionally, any of the patches shown in FIGS. 9-14 may be used in the system 82 shown in FIG. 8a.

Figures 9, 10:
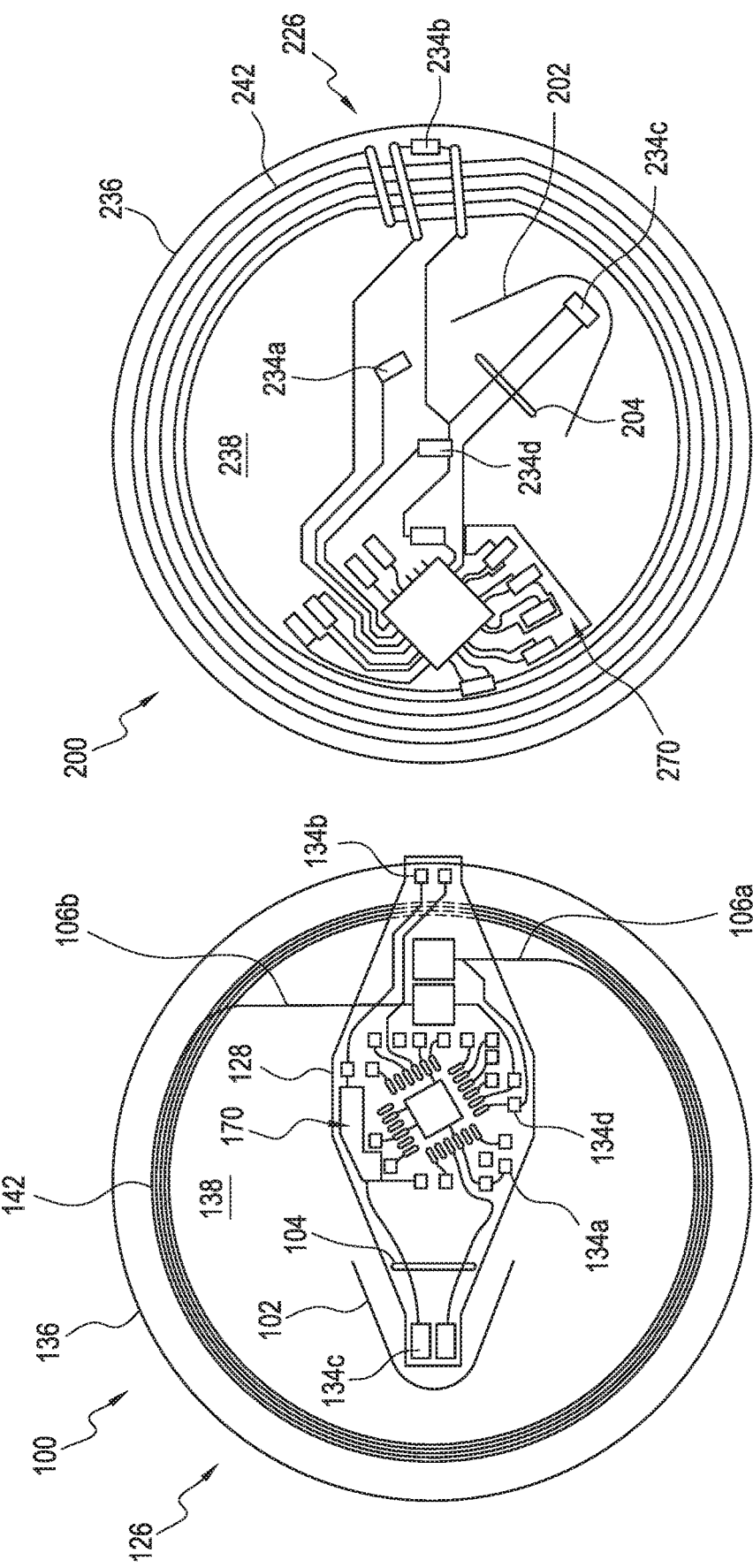
FIG. 9 illustrates a top view of components of a patch according to another example embodiment of the present disclosure.
FIG. 10 illustrates a top view of components of a patch according to yet another example embodiment of the present disclosure.

With reference to FIG. 9, in some examples a patch 100 may include a first substrate 128 and a second substrate 136 separate from the first substrate 128. In such examples, the substrate 128 may overlay and/or may be supported by the substrate 136 and, in such examples, the substrate 136 may be disposed adjacent to the substrate 128. Together, the substrates 128, 136 and/or the various components of the patch 100 disposed thereon, at least partially embedded therein, supported thereby, and/or otherwise connected thereto may comprise at least part of a flex circuit assembly 126 of the patch 100. In such embodiments, an example flex circuit assembly 126 may include, among other things, at least one sensor 134a, 134b, 134c, 134d connected to the substrate 128. Additionally, in such examples the flex circuit assembly 126 may include at least one of the sensors 134 and/or an antenna 142 connected to the substrate 136. Further, in such examples the flex circuit assembly 126 may include at least one conductive lead 106a, 106b extending from the first substrate 128 to the second substrate 136. In particular, the conductive leads 106a, 106b may extend from the antenna 142 disposed on the substrate 136 (e.g., disposed on a first side 138 of the substrate 136) to one or more components 170 of a circuit disposed on the substrate 128. For example, such a circuit may include a plurality of components 170 configured to assist in receiving, transmitting, and/or processing signals received from the sensors 134a, 134b, 134c, 134d. In example embodiments, such components 170 may include one or more microprocessors, filters, amplifiers, resistors, transistors, and/or other electronic components typically associated with known sensor control circuits. In such examples, each of the respective sensors 134a, 134b, 134c, 134d may be connected to one or more of the components 170 via additional conductive leads of the assembly 126.

As shown in FIG. 9, the substrate 136 may also include at least one cut line 102. In such examples, the cut line 102 may be a perforation and/or other cut formed into the substantially flexible material used to manufacture the substrate 136. The cut line 102 may be positioned proximate a portion of the substrate 128 including the sensor 134c. As a result, the substrate 128 may be folded substantially along a fold line 104. Folding the substrate 128 substantially along the fold line 104 may form a folded portion of the substrate 128 configured to dispose the sensor 134c connected to the substrate 128 at a location substantially overlaying the sensor 134d, 134a, or 134b. In such examples, at least a portion of the substrate 136 may be used as a layer of electrically insulative material to substantially thermally and/or electrically isolate the sensor 134c from, for example, sensor 134d. Additionally, a separate layer of electrically insulative material (not shown) similar to the layer 44 may be disposed between the sensor 134c and the sensor 134d when the substrate 128 is folded along the fold line 104.

It is understood that the sensors 134a, 134b, 134c, 134d, the antenna 142, the substrates 128, 136, and/or other components of the patch 100 may be substantially similar to the corresponding sensors 34, antenna 42, substrates 28, 36, and/or other components of the patch 10 described above. For example, the substrates 128, 136, and/or other components of the patch 100 may be made from any of the materials described above with respect to the substrates 28, 36. In particular, the substrate 136 may be made from polyester, the substrate 128 may be made from polyamide, and the antenna 142 may comprise a coil of copper or aluminum wire, etched copper or aluminum, or screened conductive ink. However, as illustrated in FIG. 9, the various components of the patch 100 may have shapes, sizes, and/or other configurations that are different from the corresponding components of the patch 10.

As shown in FIG. 10, another example patch 200 may include a single substrate 236. In such examples, the substrate 236 and the various components of the patch 200 disposed thereon, at least partially embedded therein, supported thereby, and/or otherwise connected thereto may comprise at least part of a flex circuit assembly 226 of the patch 200. In such embodiments, an example flex circuit assembly 226 may include, among other things, at least one sensor 234a, 234b, 234c, 234d connected to the substrate 236. Additionally, in such examples the flex circuit assembly 226 may include at least one antenna 242 connected to the substrate 236. While the example embodiment of FIG. 10 illustrates the sensors 234a, 234b, 234c, 234d and the antenna 242 being connected to a single side 238 of the substrate 236, in further embodiments at least one of the sensors 234a, 234b, 234c, 234d and/or the antenna 242 may be connected to an opposite side of the substrate 236.

Further, in such examples the flex circuit assembly 226 may include at least one conductive lead connecting each of the respective sensors 234a, 234b, 234c, 234d and the antenna 242 to one or more components 270 of a circuit disposed on the substrate 236. As noted above with respect to FIG. 9, such a circuit may include a plurality of components 270 configured to assist in receiving, transmitting, and/or processing signals received from the sensors 234a, 234b, 234c, 234d. In example embodiments, such components 270 may include one or more microprocessors, filters, amplifiers, resistors, transistors, and/or other electronic components typically associated with known sensor control circuits.

As shown in FIG. 10, the substrate 236 may also include at least one cut line 202. In such examples, the cut line 202 may be a perforation and/or other cut formed into the substantially flexible material used to manufacture the substrate 236. The cut line 202 may be positioned proximate a portion of the substrate 236 including the sensor 234c. As a result, the substrate 236 may be folded substantially along a fold line 204. Folding the substrate 236 substantially along the fold line 204 may form a folded portion of the substrate 236 configured to dispose the sensor 234c connected to the substrate 236 at a location substantially overlaying the sensor 234d, 234a, or 234b. In such examples, at least a portion of the substrate 236 may be used as a layer of electrically insulative material to substantially thermally and/or electrically isolate the sensor 234c from, for example, sensor 234d. Additionally, a separate layer of electrically insulative material (not shown) similar to the layer 44 may be disposed between the sensor 234c and the sensor 234d when the substrate 236 is folded along the fold line 204.

It is understood that the sensors 234a, 234b, 234c, 234d, the antenna 242, the substrate 236, and/or other components of the patch 200 may be substantially similar to the corresponding sensors 34, antenna 42, substrate 36, and/or other components of the patch 10 described above. For example, the substrate 236, and/or other components of the patch 200 may be made from any of the materials described above with respect to the substrate 36. In particular, the substrate 236 may be made from polyester or polyamide, and the antenna 242 may comprise a coil of copper or aluminum wire, etched copper or aluminum, or screened conductive ink. However, as illustrated in FIG. 10, the various components of the patch 200 may have shapes, sizes, and/or other configurations that are different from the corresponding components of the patch 10.

Figure 11:
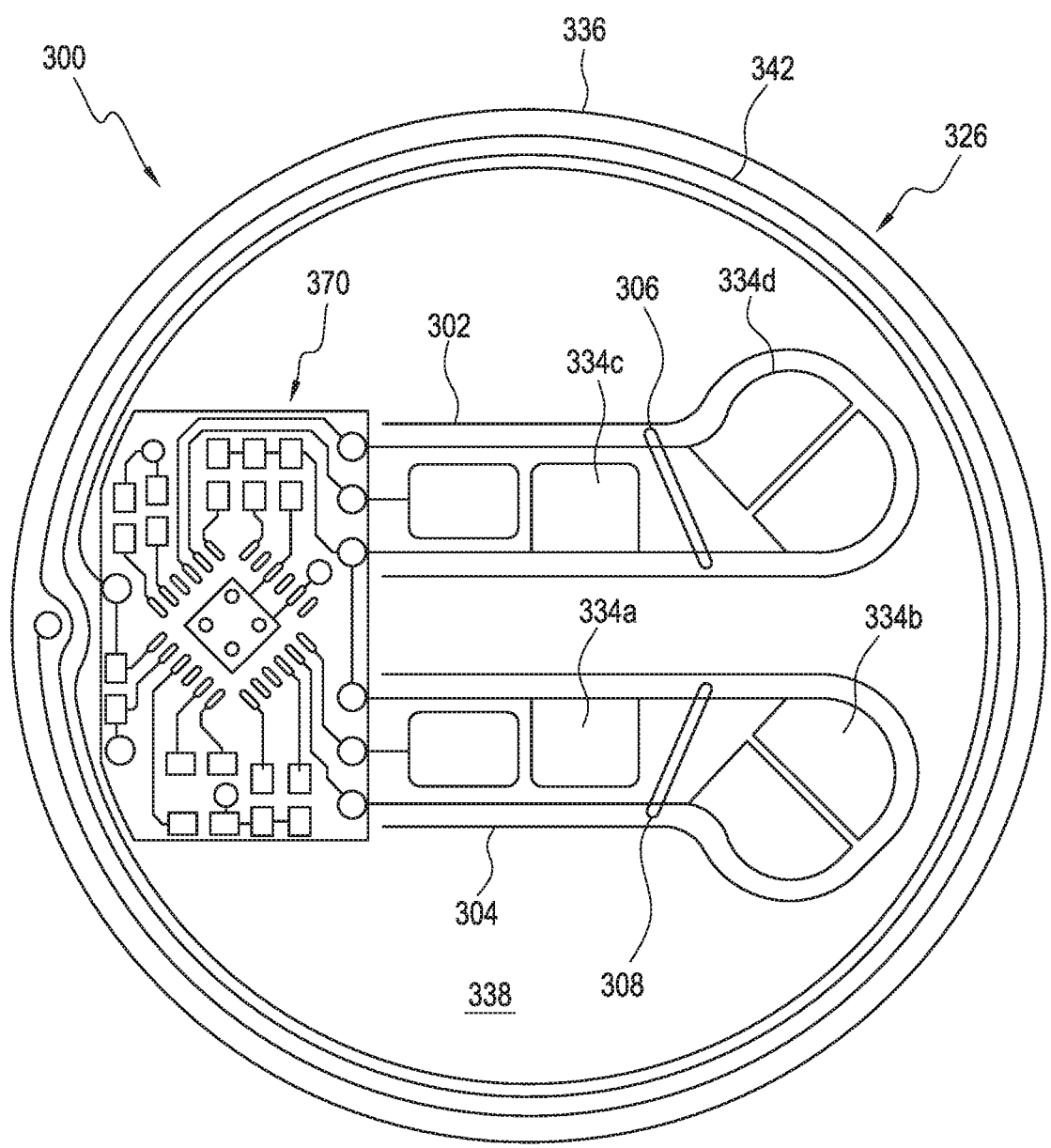
FIG. 11 illustrates a top view of components of a patch according to still another example embodiment of the present disclosure.

As shown in FIG. 11, another example patch 300 may include a single substrate 336. In such examples, the substrate 336 and the various components of the patch 300 disposed thereon, at least partially embedded therein, supported thereby, and/or otherwise connected thereto may comprise at least part of a flex circuit assembly 326 of the patch 300. In such embodiments, an example flex circuit assembly 326 may include, among other things, at least one sensor 334a, 334b, 334c, 334d connected to the substrate 336. Additionally, in such examples the flex circuit assembly 326 may include at least one antenna 342 connected to the substrate 336. While the example embodiment of FIG. 11 illustrates the sensors 334a, 334b, 334c, 334d and the antenna 342 being connected to a single side 338 of the substrate 336, in further embodiments at least one of the sensors 334a, 334b, 334c, 334d and/or the antenna 342 may be connected to an opposite side of the substrate 336.

Further, in such examples the flex circuit assembly 326 may include at least one conductive lead connecting each of the respective sensors 334a, 334b, 334c, 334d and the antenna 342 to one or more components 370 of a circuit disposed on the substrate 336. As noted above with respect to FIG. 9, such a circuit may include a plurality of components 370 configured to assist in receiving, transmitting, and/or processing signals received from the sensors 334a, 334b, 334c, 334d. In example embodiments, such components 370 may include one or more microprocessors, filters, amplifiers, resistors, transistors, and/or other electronic components typically associated with known sensor control circuits.

As shown in FIG. 11, the substrate 336 may also include at least one cut line 302, 304. In such examples, the cut lines 302, 304 may be perforations and/or other cuts formed into the substantially flexible material used to manufacture the substrate 336. As shown in FIG. 11, the cut line 302 may be positioned proximate and/or substantially surrounding a portion of the substrate 336 including one or both of the sensors 334c, 334d. Further, the cut line 304 may be positioned proximate and/or substantially surrounding a portion of the substrate 336 including one or both of the sensors 334a, 334b. As a result, the substrate 336 may be folded substantially along one or more fold lines 306, 308. Folding the substrate 336 substantially along the fold line 306 may form a folded portion of the substrate 336 configured to dispose the sensor 234c connected to the substrate 336 at a location substantially overlaying the sensor 334d or vice versa. Similarly, folding the substrate 336 substantially along the fold line 308 may form a folded portion of the substrate 336 configured to dispose the sensor 334a connected to the substrate 336 at a location substantially overlaying the sensor 334b or vice versa. In such examples, at least a portion of the substrate 336 may be used as a layer of electrically insulative material to substantially thermally and/or electrically isolate the sensor 334c from, for example, sensor 334d, and at least an additional portion of the substrate 336 may be used as another layer of electrically insulative material to substantially thermally and/or electrically isolate the sensor 334a from, for example, sensor 334b. Additionally, one or more separate layers of electrically insulative material (not shown) similar to the layer 44 may be disposed between, for example, the sensor 334c and the sensor 334d when the substrate 336 is folded along the fold line 306.

It is understood that the sensors 334a, 334b, 334c, 334d, the antenna 342, the substrate 336, and/or other components of the patch 300 may be substantially similar to the corresponding sensors 34, antenna 42, substrate 36, and/or other components of the patch 10 described above. For example, the substrate 336, and/or other components of the patch 300 may be made from any of the materials described above with respect to the substrate 36. In particular, the substrate 336 may be made from polyester or polyamide, and the antenna 342 may comprise a coil of copper or aluminum wire, etched copper or aluminum, or screened conductive ink. However, as illustrated in FIG. 11, the various components of the patch 300 may have shapes, sizes, and/or other configurations that are different from the corresponding components of the patch 10.

Figure 12:
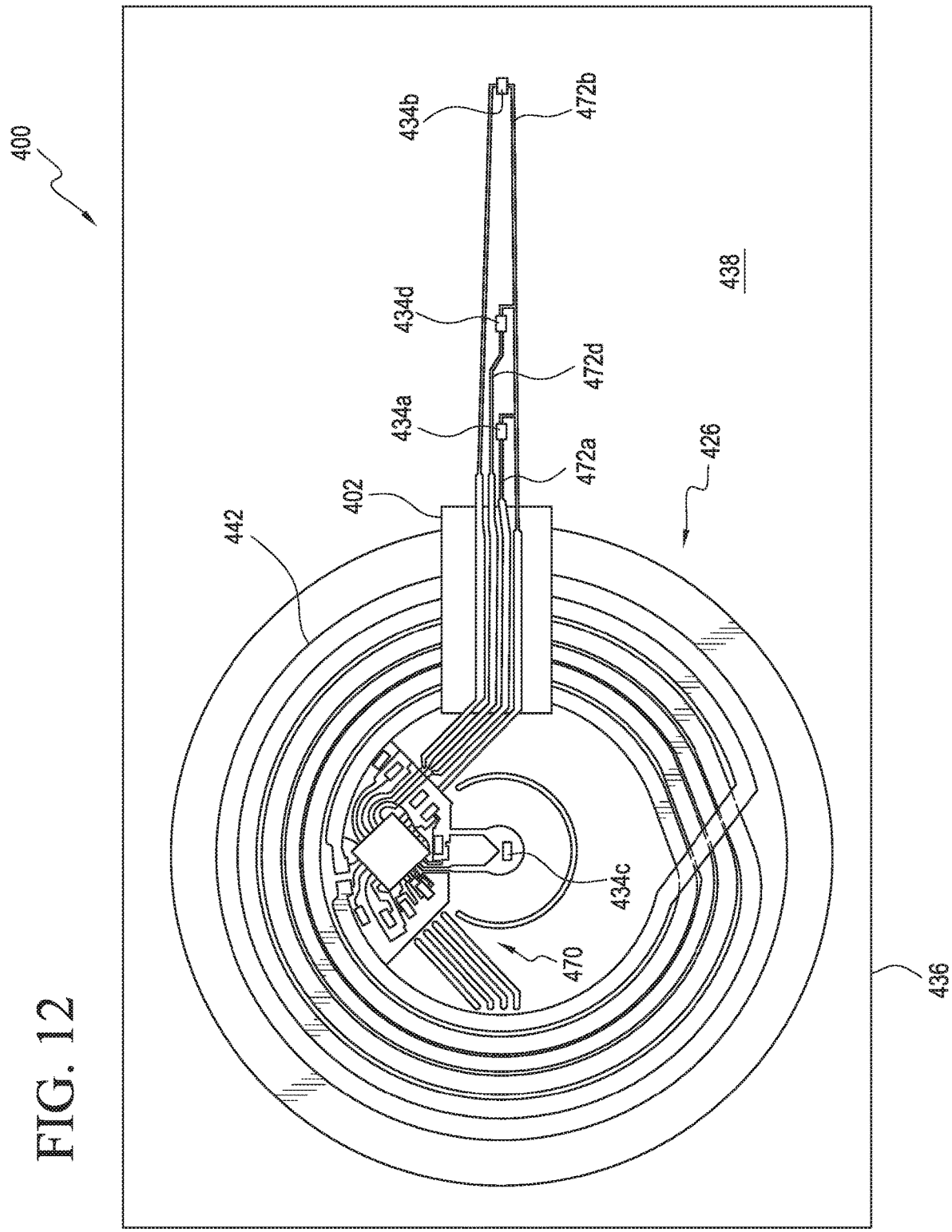
FIG. 12 illustrates a top view of components of a patch according to a further example embodiment of the present disclosure.

As shown in FIG. 12, still another example patch 400 of the present disclosure may include a substrate 436. In such examples, the substrate 436 and the various components of the patch 400 disposed thereon, at least partially embedded therein, supported thereby, and/or otherwise connected thereto may comprise at least part of a flex circuit assembly 426 of the patch 400. In such embodiments, an example flex circuit assembly 426 may include, among other things, at least one sensor 434a, 434b, 434c, 434d connected to the substrate 436. Additionally, in such examples the flex circuit assembly 426 may include at least one antenna 442 connected to the substrate 436. While the example embodiment of FIG. 12 illustrates the sensors 434a, 434b, 434c, 434d and the antenna 442 being connected to a single side 438 of the substrate 436, in further embodiments at least one of the sensors 434a, 434b, 434c, 434d and/or the antenna 442 may be connected to an opposite side of the substrate 436. For example, the substrate 436 may comprise an antenna portion and a tail portion extending from the antenna portion. In such an example embodiment the sensors 434a, 434b, 434d may be disposed on the tail portion, and the antenna 442 and the sensor 434c may be disposed on the antenna portion.

Additionally, while the example patch 400 is illustrated in FIG. 12 as including a single substrate 436, in additional embodiments such a patch 400 may include an additional substrate. For example, in such embodiments at least the sensor 434c and the antenna 442 may be disposed on the substrate 436, and at least one of the sensors 434a, 434b, 434d may be disposed on the additional substrate. Further, in such examples, the additional substrate may be disposed adjacent to the substrate 436, and at least one conductive lead may extend from the substrate 436 to the additional substrate. In such examples, the additional substrate may be positioned such that the sensor 434c substantially overlays the sensor 434d.

With continued reference to FIG. 12, the flex circuit assembly 426 may include at least one conductive lead 472a, 472b, 472c, 472d connecting each of the respective sensors 434a, 434b, 434c, 434d and/or the antenna 442 to one or more components 470 of a circuit disposed on the substrate 436. As noted above with respect to FIG. 9, such a circuit 436 may include a plurality of components 470 configured to assist in receiving, transmitting, and/or processing signals received from the sensors 434a, 434b, 434c, 434d. In example embodiments, such components 470 may include one or more microprocessors, filters, amplifiers, resistors, transistors, and/or other electronic components typically associated with known sensor control circuits.

As shown in FIG. 12, the patch 400 may also include at least layer 402 of electrically insulative material 402 positioned proximate and/or substantially overlaying a portion of the antenna 442. In some examples, the layer 402 of electrically insulative material may be disposed between the antenna 442 and the one or more conductive leads 472a, 472b, 472c, 472d. In such examples, the layer 402 may assist in reducing and/or substantially eliminating antenna interference caused by electrical current passing via the conductive leads 472a, 472b, 472c, 472d.

The example substrate 436 may be folded at a location proximate an outer perimeter of the antenna 442. Folding the substrate 436 in this way may form a folded portion of the substrate 436 configured to dispose the sensor 434c at a location substantially overlaying the sensor 434d or vice versa. In such examples, at least a portion of the substrate 436, such as a portion of the substrate 436 on which the sensor 434d is disposed, may be used as a layer of electrically insulative material to substantially thermally and/or electrically isolate the sensor 434c from, for example, sensor 434d. Additionally, one or more separate layers of electrically insulative material (not shown) similar to the layers 44, 402 may be disposed between, for example, the sensor 434c and the sensor 434d when the substrate 436 is folded as described above.

It is understood that the sensors 434a, 434b, 434c, 434d, the antenna 442, the substrate 436, and/or other components of the patch 400 may be substantially similar to the corresponding sensors 34, antenna 42, substrate 36, and/or other components of the patch 10 described above. For example, the substrate 436, and/or other components of the patch 400 may be made from any of the materials described above with respect to the substrate 36. In particular, the substrate 436 may be made from polyester or polyamide, and the antenna 442 may comprise a coil of copper or aluminum wire, etched copper or aluminum, or screened conductive ink. However, as illustrated in FIG. 12, the various components of the patch 400 may have shapes, sizes, and/or other configurations that are different from the corresponding components of the patch 10.

Figure 13:
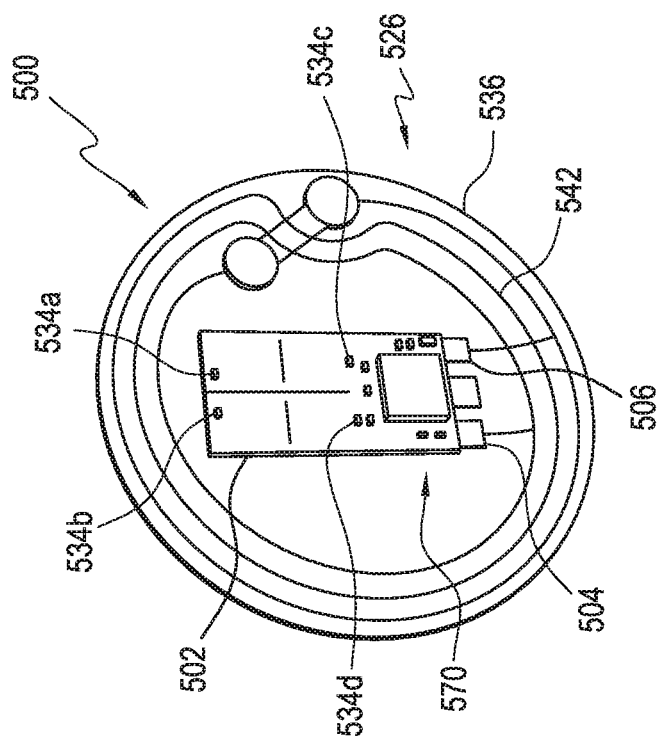
FIG. 13 illustrates a top view of components of a patch according to another example embodiment of the present disclosure.

FIG. 13 illustrates another example patch 500 of the present disclosure. As shown in FIG. 13, a patch 500 may include a first substrate 502 and a second substrate 536 separate from the first substrate 502. In such examples, the substrate 502 may overlay and/or may be supported by the substrate 536 and, in such examples, the substrate 536 may be disposed adjacent to the substrate 502. Together, the substrates 502, 536 and/or the various components of the patch 500 disposed thereon, at least partially embedded therein, supported thereby, and/or otherwise connected thereto may comprise at least part of a flex circuit assembly 526 of the patch 500. In such embodiments, an example flex circuit assembly 526 may include, among other things, at least one sensor 534a, 534b, 534c, 534d connected to the substrate 502. Additionally, in such examples the flex circuit assembly 526 may include at least one of the sensors 534a, 534b, 534c, 534d and/or an antenna 542 connected to the substrate 536. Further, in such examples the flex circuit assembly 526 may include at least one conductive lead extending from respective terminals 504, 506 of the substrate 502 to the antenna 542. In particular, the conductive leads may extend from the antenna 542 disposed on the substrate 536 to the respective terminals 504, 506, and the terminals 504, 506 may connect the antenna 542 to one or more components 570 of a circuit disposed on the substrate 502. For example, such a circuit may include a plurality of components 570 configured to assist in receiving, transmitting, and/or processing signals received from the sensors 534a, 534b, 534c, 534d. In example embodiments, such components 570 may include one or more microprocessors, filters, amplifiers, resistors, transistors, and/or other electronic components typically associated with known sensor control circuits. In such examples, each of the respective sensors 534a, 534b, 534c, 534d may be connected to one or more of the components 570 via additional conductive leads of the substrate 502. For example, the sensors 534a, 534b, 534c, 534d and the components 570 may be connected to the substrate 502 as is commonly done with electrical components of known printed circuit boards. In such examples, the components 570 disposed on the substrate 502 may comprise a pre-packaged bundle of electrical components that may be easily connected to the substrate 502 during manufacturing of the patch 500. As a result, the cost and complexity of manufacturing the patch 500 may be reduced relative to known patches.

It is understood that the sensors 534a, 534b, 534c, 534d, the antenna 542, the substrates 502, 536, and/or other components of the patch 500 may be substantially similar to the corresponding sensors 34, antenna 42, substrates 28, 36, and/or other components of the patch 10 described above. For example, the substrates 502, 536, and/or other components of the patch 500 may be made from any of the materials described above with respect to the substrates 28, 36. In particular, the substrate 536 may be made from polyester, the substrate 502 may be made from polyamide, and the antenna 542 may comprise a coil of copper or aluminum wire, etched copper or aluminum, or screened conductive ink. However, as illustrated in FIG. 13, the various components of the patch 500 may have shapes, sizes, and/or other configurations that are different from the corresponding components of the patch 10.

Figure 14:
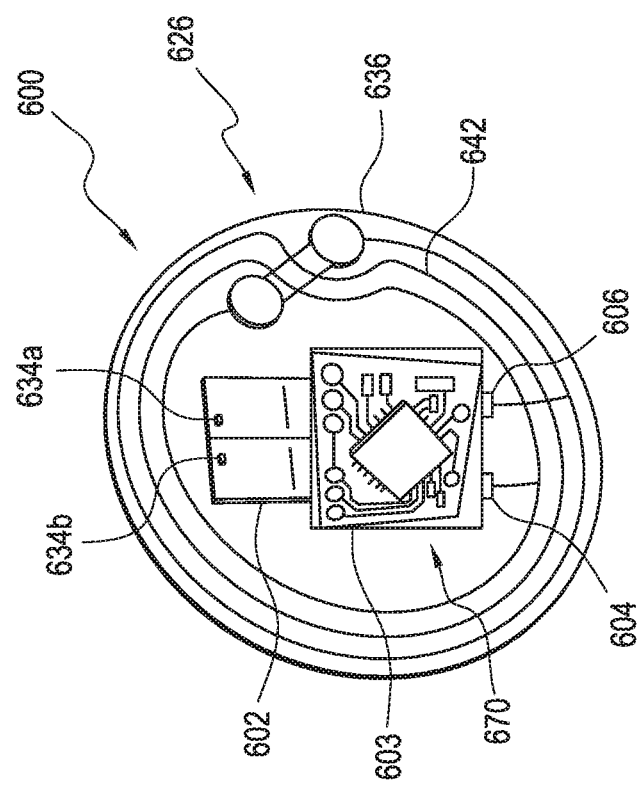
FIG. 14 illustrates a top view of components of a patch according to still another example embodiment of the present disclosure.

FIG. 14 illustrates still another example patch 600 of the present disclosure. As shown in FIG. 14, a patch 600 may include a first substrate 602 and a second substrate 636 separate from the first substrate 602. In such examples, the substrate 602 may overlay and/or may be supported by the substrate 636 and, in such examples, the substrate 636 may be disposed adjacent to the substrate 602. Together, the substrates 602, 636 and/or the various components of the patch 600 disposed thereon, at least partially embedded therein, supported thereby, and/or otherwise connected thereto may comprise at least part of a flex circuit assembly 626 of the patch 500. In such embodiments, an example flex circuit assembly 626 may include, among other things, at least one sensor 634a, 634b, 634c, 634d connected to the substrate 602. Additionally, in such examples the flex circuit assembly 626 may include at least one of the sensors 634a, 634b, 634c, 634d and/or an antenna 642 connected to the substrate 636. Further, in such examples the flex circuit assembly 626 may include at least one conductive lead extending from respective terminals 604, 606 of the substrate 602 to the antenna 642.

In particular, the conductive leads may extend from the antenna 642 disposed on the substrate 636 to the respective terminals 604, 606, and the terminals 604, 606 may connect the antenna 642 to one or more components 670 of a circuit disposed on a third substrate 603. For example, such a circuit may include a plurality of components 670 configured to assist in receiving, transmitting, and/or processing signals received from the sensors 634a, 634b, 634c, 634d. In example embodiments, such components 670 may include one or more microprocessors, filters, amplifiers, resistors, transistors, and/or other electronic components typically associated with known sensor control circuits. In some examples, the components 670 disposed on the substrate 603 may comprise an FR4 flip chip that is configured to control operation of and/or condition one or more signals received from the respective sensors 634a, 634b, 634c, 634d located on the substrate 602. In such examples, each of the respective sensors 634a, 634b, 634c, 634d may be connected to one or more of the components 670 disposed on the substrate 603 via additional conductive leads and/or conductive terminals connecting the substrate 603 with the substrate 602.

It is understood that the sensors 634a, 634b, 634c, 634d, the antenna 642, the substrates 602, 603, 636, and/or other components of the patch 600 may be substantially similar to the corresponding sensors 34, antenna 42, substrates 28, 36, and/or other components of the patch 10 described above. For example, the substrates 602, 603, 636, and/or other components of the patch 600 may be made from any of the materials described above with respect to the substrates 28, 36. In particular, the substrate 636 may be made from polyester, the substrates 602, 603 may be made from polyamide, and the antenna 542 may comprise a coil of copper or aluminum wire, etched copper or aluminum, or screened conductive ink. However, as illustrated in FIG. 14, the various components of the patch 600 may have shapes, sizes, and/or other configurations that are different from the corresponding components of the patch 10.

Based on the descriptions included herein, it is understood that the example patches and/or systems of the present disclosure may be used in any desired patient monitoring process. For example, such example patches and/or systems may be used to determine and/or monitor a temperature (e.g., a core temperature) of the patient 86. By way of a nonlimiting example involving the system 82 and the patch 10 described herein, FIG. 15 shows a flow chart 700 illustrating an example method of the present disclosure. As shown in FIG. 15, an example method of determining a temperature of a patient may include, among other things, at step 702, removing the release liner 12 from the nonwoven layer 18, and, at step 704, removably attaching the patch 10 to a skin surface 94 of the patient 86 such that the visual indicia 56 extends substantially parallel to a blood vessel 84 of the patient 86 disposed beneath the skin surface 94.

The method may also include, at step 706, determining a first temperature of the skin surface 94 of the patient 86 with the temperature sensor 34a, determining, at step 708, a second temperature of the skin surface 94 with the temperature sensor 34b, determining, at step 710, a third temperature of the skin surface 94 with the temperature sensor 34d, and determining, at step 712, a fourth temperature of the skin surface 94 with the temperature sensor 34c. In such examples, it is understood that the temperature sensor 34c may be disposed at a location on the patch 10 substantially overlaying the temperature sensor 34d. Additionally, each of the temperature sensors 34a, 34b, 34c, 34d may be connected to the first substrate 28 of the patch 10, while an antenna 42 of the patch 10 may be connected to a second substrate 36 of the patch 10 disposed adjacent to the first substrate 28. Further, the first, second, third, and fourth temperatures described above may be determined substantially simultaneously, and while the patch 10 is removably attached to and/or otherwise disposed on the skin surface 94.

Such a temperature determination method may also include, at step 714, determining a correction factor based at least in part one or more of the first, second, third, and fourth temperatures discussed above. For example, as described above with respect to FIG. 8 one or more differences between the temperatures determined by the respective sensors 34a, 34b, 34c, 34d may be used by the controller 90 and/or by a controller or other component 70 of the circuit 69 disposed on the patch 10 to determine such a correction factor at step 714. In some examples, the patch 10 and/or the various sensors 34a, 34b, 34c, 34d associated therewith may be calibrated prior to use. Such a calibration process may include, for example, determining one or more temperatures of a known calibration apparatus. For example, during such a process the patch 10 may be removably attached to a calibration apparatus having a shape, size, and/or other configuration similar to a limb of a patient. The calibration apparatus may have a known temperature, and each of the sensors 34a, 34b, 34c, 34d may measure a respective temperature of the calibration apparatus. The differences between the known temperature and the respective temperatures determined by the sensors 34a, 34b, 34c, 34d during the calibration process may be stored in, for example, a memory associated with the controller 90, and may be used as offsets during temperature determination methods in which the sensors 34a, 34b, 34c, 34d are used. In some examples, such offsets may be used in addition to and/or in place of the correction factor when determining the temperature of the patient. For example, one or more such offsets may be used as an input to a patient temperature determination algorithm.

The method may also include determining, at step 716, a temperature of the patient 86 based at least in part on the correction factor and based at least in part on one or more of the first, second, third, and fourth temperatures. For example, at step 716 the controller 90 and/or a controller or other component 70 of the circuit 69 may use one or more of the first, second, third, and fourth temperatures, and/or the correction factor as inputs into one or more patient temperature determination algorithms (e.g., core temperature determination algorithms). As noted above, additionally or alternatively one or more temperature offsets associated with the respective sensors 34a, 34b, 34c, 34d may be used as an input to such patient temperature determination algorithms at step 716.

In such examples, equation [1] below can be used by the controller 90 and/or by components 70 of the patch 10 to calculate a temperature of the patient 86:

$$T_{patient} = T_1 + R(T_1 - T_2) + CF. \quad [1]$$

In the above equation, $T_1$ may be a skin surface temperature measured by the temperature sensor 34d, $T_2$ may be a skin surface temperature measured by the temperature sensor 34c, and R may be a dynamic thermal resistance of a skin layer associated with the skin surface 94 on which the patch 10 is disposed. Additionally, the correction factor "CF" may compensate for heat flow (stray conduction) caused by blood flow moving through the skin layer, as well as the various differences in temperature determined by the sensors 34. In some examples, such a correction factor CF may be an empirically derived constant.

Additionally, at step 718. the controller 90 and/or a controller or other component 70 of the circuit 69 may output the determined temperature via the user interface 88. For example, the controller or other component 70 of the circuit 69 may transmit signals indicative of the first, second, third, and fourth temperatures to the controller 90 using the antenna 42. The controller 90 may then determine the patient temperature as described above, and may display and/or otherwise provide the determined temperature via a display and/or other component of user interface 88.

Additionally, and/or alternatively, in any of the examples described herein the controller 90 may utilize the skin surface temperatures determined by the sensors 34 or differences between such skin surface temperatures as inputs into one or more lookup tables, charts, neural networks, and/or other controller components in determining a thermal resistance of the skin layer, the correction factor noted above, and/or any other parameters. By utilizing a variety of different skin surface temperatures determined by sensors disposed at various positions on the patch 10, and by incorporating known thermal resistance values of the patch and/or correction factors into the determination of patient temperature, the accuracy of the temperature determinations described herein may be improved.

In still further examples, patient demographic data (e.g., age, ethnicity, body mass index, measurement site, etc.) may be used to determine any of the patient temperatures described herein. For example, one or more such data may impact (e.g., increase or decrease) the thermal resistance of the skin layer associated with the skin surface on which the patch 10 is disposed. As a result, one or more such data may be used as an input into one or more lookup tables, charts, neural networks, and/or other controller components in determining a thermal resistance of the skin layer, the correction factor noted above, and/or any other parameters. By using such data, or one or more values indicative of such data, in the calculations described above, the accuracy of the temperature determinations described herein may be further improved.

FIG. 16 shows a flowchart 800 illustrating still another example method of the present disclosure. As shown in FIG. 16, such an example method (e.g., a method of manufacturing a patch of the present disclosure) may include, at step 802, providing a substrate including a longitudinal axis A, a first side, and a second side opposite the first side. The method may also include, at step 804, connecting a first temperature sensor 34a to the substrate along the longitudinal axis A, connecting, at step 806, a second temperature sensor 34b to the substrate along the longitudinal axis A and spaced from the first temperature sensor 34a. The method may also include, at step 808, connecting a third temperature sensor 34d to the substrate along the longitudinal axis A between the first temperature sensor 34a and the second temperature sensor 34b. Further, the method may include, at step: 810, providing a fourth temperature sensor 34c substantially overlaying the third temperature sensor 34d. In some examples, the substrate provided at step 802 may comprise a first substrate 28 of a patch 10, and the method illustrated by the flow chart 800 may further include providing a second substrate 36. In such examples, one or more of the sensors 34 described above may be connected to the first substrate 28 or to the second substrate 36 at steps 804-810.

As shown in FIG. 16, an example method may also include providing, at step: 812, an antenna 42 at a fixed location relative to the substrate. In some examples, the antenna 42 may be connected to the substrate 28, while in other examples, the antenna 42 may be connected to the substrate 36. The antenna 42 provided at step 812 may be configured to transmit information associated with temperatures determined by one or more of the temperature sensors 34. At step: 814, the method may further include connecting (e.g., operably connecting) a controller to one or more of the temperature sensors 34. In some examples, the controller may be configured to determine a correction factor based on temperatures determined by at least two of the temperature sensors 34, and to determine a patient temperature based on the correction factor and the temperatures determined by the at least two of the temperature sensors 34.

As noted above, some methods of the present disclosure may include providing two substrates 28, 36. In such example methods, each of the temperature sensors 34 noted above with respect to steps: 804-810 may be connected to a side of the first substrate 28, and the antenna provided at step: 812 may be connected to a side of the second substrate 36. In such example methods, a layer of electrically insulative material may be provided, and such material may space at least the fourth temperature sensor 34c from the third temperature sensor 34d. Such example methods may also include forming a folded portion 68 of the first substrate 28 positioning the various temperature sensors 34 such that the fourth temperature 34c sensor substantially overlays the third temperature sensor 34d.

Additionally, any of the methods described herein may include, at step: 816, connecting at least part of the substrate provided at step 802 to a nonwoven layer 18. Additionally, such methods may include, at step: 818, removably attaching a release liner 12 to the nonwoven layer 18, such as with one or more layers of adhesive.

The invention has been described in detail with particular reference to a presently preferred embodiment, but it will be understood that variations and modifications can be effected within the spirit and scope of the invention. The presently disclosed embodiments are, therefore, considered in all respects to be illustrative and not restrictive. The scope of the invention is indicated by the appended claims, and all changes that come within the meaning and range of equivalents thereof are intended to be embraced therein.

The invention claimed is:

1. A wearable patch, comprising:
   a substrate having a first surface and a second surface opposite the first surface;
   a plurality of temperature sensors, including:
      a first temperature sensor connected to the substrate and disposed along a longitudinal axis of the substrate,
      a second temperature sensor connected to the substrate, disposed along the longitudinal axis, and spaced from the first temperature sensor,
      a third temperature sensor connected to the substrate, and disposed along the longitudinal axis between the first temperature sensor and the second temperature sensor, and
      a fourth temperature sensor, the third temperature sensor and the fourth temperature sensor being:
         connected to the first surface of the substrate, and
         disposed along a transverse axis extending substantially perpendicular to the longitudinal axis;
   a layer of electrically insulative material spacing the fourth temperature sensor from the third temperature sensor; and
   an antenna configured to transmit information associated with temperatures determined by the first, second, third, and fourth temperature sensors.

2. The patch of claim 1, wherein the substrate comprises a first substrate, the first surface comprises a a first side of the first substrate, and the second surface comprises a second side of the first substrate opposite the first side,
   the patch further comprising a second substrate having a third side and a fourth side opposite the third side,
   the fourth temperature sensor being connected to the first substrate, and
   the antenna being connected to the second substrate.

3. The patch of claim 2, wherein:
   the fourth side of the second substrate faces at least part of the first side of the first substrate,
   the first, second, third, and fourth temperature sensors are disposed on the second side of the first substrate, and
   the antenna is disposed on the third side of the second substrate.

4. The patch of claim 3, wherein the first substrate includes:
   a first portion extending along the fourth side of the second substrate and including the third temperature sensor,
   a second portion including the fourth temperature sensor, and
   a folded portion disposed between the first portion and the second portion, the folded portion positioning the second portion such that the fourth temperature sensor substantially overlays the third temperature sensor.

5. The patch of claim 4, further comprising a cover layer connected to the second side of the first substrate, the cover layer overlaying the fourth temperature sensor and at least part of the second portion.

6. The patch of claim 5, wherein the cover layer includes visual indicia indicting a preferred orientation of the patch relative to a blood vessel of a patient.

7. The patch of claim 2, wherein the layer of electrically insulative material is disposed on the third side of the second substrate, and is positioned to overlay the first and third temperature sensors, but not to overlay the second temperature sensor.

8. The patch of claim 2, further comprising a nonwoven layer having a fifth side and a sixth side opposite the fifth side,
   the fifth side being connected to at least part of the fourth side of the second substrate, and
   the sixth side being removably attachable to a skin surface of a patient.

9. The patch of claim 8, wherein the nonwoven layer includes an opening extending from the fifth side to the sixth side, the first substrate being positioned such that the first, second, and third temperature sensors are facing and substantially overlay the opening.

10. The patch of claim 8, further comprising adhesive disposed on the sixth side of the nonwoven layer, the sixth side including a plurality of areas in which substantially none of the adhesive is disposed.

11. The patch of claim 8, further comprising a release liner removably attached to the sixth side of the nonwoven layer, the nonwoven layer further comprising a grip extending proximal to the first and second substrates.

12. The patch of claim 1, wherein the first surface of the substrate comprises a first substantially planar surface, and the second surface of the substrate comprises a second substantially planar surface.

13. The patch of claim 12, wherein at least part of the antenna is disposed between a first portion of the second surface and a second portion of the second surface facing the first portion.

14. A wearable patch, comprising:
a substrate including a first surface and a second surface opposite the first surface,
a plurality of temperature sensors, including:
a first temperature sensor connected to the first surface of the substrate and disposed along a longitudinal axis of the substrate
a second temperature sensor connected to the first surface of the substrate, disposed along the longitudinal axis, and spaced from the first temperature sensor,
a third temperature sensor connected to the first surface of the substrate, and disposed along the longitudinal axis between the first temperature sensor and the second temperature sensor, and
a fourth temperature sensor connected to the first surface of the substrate,
the third temperature sensor and the fourth temperature sensor being disposed along a transverse axis extending substantially perpendicular to the longitudinal axis;
a layer of electrically insulative material spacing the fourth temperature sensor from the third temperature sensor; and
an antenna configured to transmit information associated with temperatures determined by the first, second, third, and fourth tempereature sensors.

15. The patch of claim 14, wherein at least part of the antenna is disposed between a first portion of the second surface and a second portion of the second surface facing the first portion.

16. A wearable patch, comprising:
a substrate including a first surface and a second surface opposite the first surface;
a plurality of temperature sensors, including:
a first temperature sensor connected to the substrate and disposed along a longitudinal axis of the substrate,
a second temperature sensor connected to the first surface of the substrate, and disposed along the longitudinal axis between the first temperature sensor and the substrate,
a third temperature sensor connected to the first surface of the substrate, and disposed along the longitudinal axis between the first temperature sensor and the second temperature sensor, and
a fourth temperature sensor connected to the first surface of the substrate,
wherein the third temperature sensor is disposed in a first plane including the longitudinal axis, and the fourth temperature sensor is disposed in a second plane axially spaced from the first plane;
a layer of electrically insulative material spacing the fourth temperature sensor from the third temperature sensor; and
an antenna configured to transmit information associated with temperatures determined by the first, second, third, and fourth temperature sensors, at least part of the antenna being disposed between a first portion of the second surface and a second portion of the second surface facing the first portion.

* * * * *